US012646624B2

(12) United States Patent
Bharmi et al.

(10) Patent No.: US 12,646,624 B2
(45) Date of Patent: Jun. 2, 2026

(54) CLINICAL DECISION SUPPORT FOR CHRONIC PAIN MANAGEMENT

(71) Applicant: Medtronic, Inc., Minneapolis, MN (US)

(72) Inventors: Rupinder Bharmi, Canyon Country, CA (US); Noa Lempel, Hod Hasharon (IL); Roy Amit, Tel Aviv (IL); Filippo Coletti, Terni (IT); Charisma Sana Kumar, Edina, MN (US); Ashwini Dayal Sharan, Pennington, NJ (US); Malgorzata Maria Straka, Blaine, MN (US); Joshua James Nedrud, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/786,262

(22) Filed: Jul. 26, 2024

(65) Prior Publication Data

US 2025/0037867 A1     Jan. 30, 2025

Related U.S. Application Data

(60) Provisional application No. 63/529,344, filed on Jul. 27, 2023.

(51) Int. Cl.
| | |
|---|---|
| *G16H 50/30* | (2018.01) |
| *G16H 10/20* | (2018.01) |
| *G16H 50/20* | (2018.01) |
| *G16H 10/60* | (2018.01) |

(52) U.S. Cl.
CPC ............. *G16H 50/20* (2018.01); *G16H 10/20* (2018.01); *G16H 50/30* (2018.01); *G16H 10/60* (2018.01)

(58) Field of Classification Search
None
See application file for complete search history.

(56) References Cited

U.S. PATENT DOCUMENTS

| | | | |
|---|---|---|---|
| 2002/0128866 A1 | 9/2002 | Goetzke et al. | |
| 2015/0332020 A1 | 11/2015 | Lo et al. | |

(Continued)

FOREIGN PATENT DOCUMENTS

| | | | | | |
|---|---|---|---|---|---|
| WO | WO-2023064315 A1 * | 4/2023 | ............. | G16H 80/00 |
| WO | WO-2024200244 A1 * | 10/2024 | ............. | G16H 40/67 |

OTHER PUBLICATIONS

"PROMIS Adult Profile Instruments Scoring Manual"; PROMIS; Sep. 10, 2021 (Year: 2021).*

(Continued)

*Primary Examiner* — John A Pauls
(74) *Attorney, Agent, or Firm* — Sheridan Ross P.C.

(57) ABSTRACT

Methods, systems, and devices include processing one or more inputs including at least one of patient-provided answers and device utilization information in association with at least one health domain, wherein the at least one health domain is associated with one or more chronic conditions, determining one or more states of a patient in association with the at least one health domain based at least in part on processing the one or more inputs, and storing information describing the one or more states in an electronic data record.

20 Claims, 28 Drawing Sheets
(22 of 28 Drawing Sheet(s) Filed in Color)

(56) References Cited

U.S. PATENT DOCUMENTS

| 2017/0372018 A1 | 12/2017 | Rosenblatt et al. | |
| 2024/0293677 A1* | 9/2024 | Netoff | A61N 1/365 |

OTHER PUBLICATIONS

"A Retrospective, Multicenter, Quantitative Analysis of Patients' Baseline Pain Quality (PROMIS-29) Entering into Pain and Spine Practices in the United States (ALIGN)"; Pope et al.; Feb. 23, 2021 (Year: 2021).*

"National Coverage Determination (NCD) Electrical Nerve Stimulators," Centers for Medicare & Medicaid Services, 1995, 2 pages [retrieved online Dec. 12, 2024 from: www.cms.gov/medicare-coverage-database/view/ncd.aspx?NCDId=240].

"Place of Service Codes for Professional Claims," U.S. Centers for Medicare & Medicaid Services, updated Dec. 21, 2021, 10 pages [retrieved online May 20, 2023 from: www.cms.gov/Medicare/Coding/place-of-service-codes/Place_of_Service_Code_Set].

"PROMIS® Score Cut Points," Northwestern University, as of Mar. 21, 2023, 11 pages [retrieved online Dec. 11, 24 from: web.archive.org/web/20230321153331/https://www.healthmeasures.net/score-and-interpret/interpret-scores/promis/promis-score-cut-points].

Andre et al. "Trial designs using real-world data: The changing landscape of the regulatory approval process," Pharmacoepidemiology and Drug Safety, 2020, vol. 29, No. 10, pp. 1201-1212.

Arnott et al. "Exploring the Experiences and Perceptions of Participating in a Peer Support Intervention for Adults with Chronic Non-cancer Pain: a qualitative systematic review," JBI Evidence Synthesis, 2023, vol. 21, No. 8, 63 pages.

Benjamini et al. "Controlling the False Discovery Rate: A Practical and Powerful Approach to Multiple Testing," Journal of the Royal Statistical Society Series B (Methodological), 1995, vol. 57, No. 1, pp. 289-300.

Venkatraman et al. "Real World Characterization of Chronic Pain, Success Rates and Implant Rates: Evidence from a Digital Health Platform of Patients Undergoing Spinal Cord Stimulation Evaluations," The Journal of Pain, Dec. 2023, vol. 24, No. 12, pp. 2228-2239.

Bijur et al. "Reliability of the visual analog scale for measurement of acute pain," Academic Emergency Medicine, Dec. 2001, vol. 8, No. 12, pp. 1153-1157.

Blonde et al. "Interpretation and Impact of Real-World Clinical Data for the Practicing Clinician," Advances in Therapy, 2018, vol. 35, No. 11, pp. 1763-1774.

Cella et al. "Setting standards for severity of common symptoms in oncology using the PROMIS item banks and expert judgment," Quality of Life Research, 2014, vol. 23, No. 10, pp. 2651-2661.

Cella et al. "What is Assessment Center," assessmentcenter.net, 2013, 1 page [retrieved online Dec. 11, 2024 from: www.assessmentcenter.net].

Cella et al. "PROMIS(R) Adult Health Profiles: Efficient Short-Form Measures of Seven Health Domains," Value Health, May 2019, vol. 22, No. 5, pp. 537-544.

Chadwick et al. "To Trial or Not to Trial Before Spinal Cord Stimulation for Chronic Neuropathic Pain: The Patients' View From the TRIAL-STIM Randomized Controlled Trial," Neuromodulation: Technology at the Neural Interface, 2021, vol. 24, No. 3, pp. 459-470.

Colloca et al. "Neuropathic pain," Nature Reviews Disease Primers, 2017, vol. 3, article 17002, 19 pages.

Dahlhamer et al. "Prevalence of Chronic Pain and High-Impact Chronic Pain Among Adults—United States, 2016," Morbidity and Mortality Weekly Report, Sep. 14, 2018, vol. 67, No. 36, pp. 1001-1006.

Daniels et al. "Perioperative Management of Spinal Cord Stimulators and Intrathecal Pain Pumps," Journal of the American Academy of Orthopaedic Surgeons, Sep. 2022, vol. 30, No. 17, pp. e1095-e1105.

Deyo et al. "Opioids for low back pain," BMJ, Jan. 2015, vol. 350, article g6380, 43 pages.

Druce et al. "Maximizing Engagement in Mobile Health Studies: Lessons Learned and Future Directions," Rheum Dis Clin North Am., 2019, vol. 45, No. 2, pp. 159-172.

Dunbar et al. "Longitudinal Associations of PROMIS-29 Anxiety and Depression Symptoms With Low Back Pain Impact in a Sample of U.S. Military Service Members," Military Medicine, Mar./Apr. 2023, vol. 188, pp. e630-e636.

Eldabe et al. "Does a screening trial for spinal cord stimulation in patients with chronic pain of neuropathic origin have clinical utility and cost-effectiveness (TRIAL-STIM)? A randomised controlled trial." Pain, 2020, vol. 161, No. 12, pp. 2820-2829.

Feldman et al. "Pain, negative mood, and perceived support in chronic pain patients: a daily diary study of people with reflex sympathetic dystrophy syndrome," Journal of Consulting and Clinical Psychology, 1999, vol. 67, No. 5, pp. 776-785.

Fishman et al. "Prospective, Multicenter Feasibility Study to Evaluate Differential Target Multiplexed Spinal Cord Stimulation Programming in Subjects With Chronic Intractable Back Pain With or Without Leg Pain," Pain Pract, 2020, vol. 20, No. 7, pp. 761-768.

Grider et al. "Effectiveness of spinal cord stimulation in chronic spinal pain: A systematic review," Pain Physician, 2016, vol. 19, No. 1, pp. E33-E54.

Hatheway et al. "Long-Term Efficacy of a Novel Spinal Cord Stimulation Clinical Workflow Using Kilohertz Stimulation: Twelve-Month Results From the Vectors Study," Neuromodulation: Technology at the Neural Interface, 2021, vol. 24, No. 3, pp. 556-565.

Hays et al. "PROMIS(®)-29 v2.0 profile physical and mental health summary scores," Quality of Life Research, 2018, vol. 27, No. 7, pp. 1885-1891.

HealthMeasures "HealthMeasures Scoring Service—Scoring PROMIS Global, Profiles, and Psychosocia Illness Impact," YouTube, Aug. 24, 2016, 6 pages (transcript only) [retrieved online Dec. 12, 2024 from: www.youtube.com/watch?v=KM2FqYoS--A].

Hussaini et al. "Specialty-Based Variations in Spinal Cord Stimulation Success Rates for Treatment of Chronic Pain," Neuromodulation: Technology at the Neural Interface, 2017, vol. 20, No. 4, pp. 340-347.

Institute of Medicine, "Relieving Pain in America: A Blueprint for Transforming Prevention, Care, Education, and Research," Washington (DC): National Academies Press, © 2011, 383 pages.

Kapural et al. "Novel 10-KHz High-frequency Therapy (HF10 Therapy) is Superior to Traditional Low-frequency Spinal Cord Stimulation for the Treatment of Chronic Back and Leg Pain: The SENZA-RCT Randomized Controlled Trial," Anesthesiology, Oct. 2015, vol. 123, No. 4, pp. 851-860.

Karcioglu et al. "A systematic review of the pain scales in adults: Which to use?" American Journal of Emergency Medicine, 2018, vol. 36, No. 4, pp. 707-714.

Khutok et al. "Responsiveness of the PROMIS-29 Scales in Individuals With Chronic Low Back Pain," Spine, 2020, vol. 46, No. 2, pp. 107-113.

Levandowsky et al. "Distance between Sets," Nature. Sep. 1972, vol. 239, p. 174.

Liu et al. "Real-world data: a brief review of the methods, applications, challenges and opportunities," BMC Medical Research Methodology, 2022, vol. 22, No. 1, article 287, 10 pages.

Lunde et al. "Long-term follow-up with a smartphone application improves exercise capacity post cardiac rehabilitation: A randomized controlled trial," European Journal of Preventive Cardiology, 2020, vol. 27, No. 16, pp. 1782-1792.

Mills et al. "Chronic pain: a review of its epidemiology and associated factors in population-based studies," British Journal of Anaesthesia, 2019, vol. 123, No. 2, pp. e273-e283.

Moens et al. "Heart rate variability is not suitable as a surrogate marker for pain intensity in patients with chronic pain," Pain, Aug. 2023, vol. 164, No. 8, pp. 1741-1749.

Murphy et al. "The Volume-Outcome Effect: Impact on Trial-to-Permanent Conversion Rates in Spinal Cord Stimulation," Neuromodulation: Technology at the Neural Interface, 2017, vol. 20, No. 3, pp. 256-262.

(56)        References Cited

OTHER PUBLICATIONS

NIELSEN "Hierarchical Clustering," Springer, 2016, In Introduction to HPC with MPI for Data Science, Chapter 8, pp. 195-211.

O'Brien et al. "Negative mood mediates the effect of poor sleep on pain among chronic pain patients," The Clinical Journal of Pain, May 2010, vol. 26, No. 4, pp. 310-319.

Patel et al. "PROMIS Physical Function for prediction of postoperative pain, narcotics consumption, and patient-reported outcomes following minimally invasive transforaminal lumbar interbody fusion," Journal of Neurosurgery: Spine, 2019, vol. 30, pp. 476-482.

Patterson et al. "Objective wearable measures correlate with self-reported chronic pain levels in people with spinal cord stimulation systems," NPJ Digital Medicine, Aug. 2023, vol. 6, Article 146, 9 pages.

Perrot et al. "Are there risk factors for musculoskeletal procedural pain? A national prospective multicentre study of procedural instantaneous pain and its recall after knee and spine injections," Joint Bone Spine, 2011, vol. 78, No. 6, pp. 629-635.

Petersen et al. "Effect of High-frequency (10-kHz) Spinal Cord Stimulation in Patients With Painful Diabetic Neuropathy: A Randomized Clinical Trial." JAMA Neurology, Jun. 2021, vol. 78, No. 6, pp. 687-698.

Ponder et al. "A Smartphone App With a Digital Care Pathway for Patients Undergoing Spine Surgery: Development and Feasibility Study," JMIR Perioperative Medicine, 2020, vol. 3, No. 2, article e21138, 16 pages.

Ponder et al. "Mobile Health Application for Patients Undergoing Breast Cancer Surgery: Feasibility Study," JCO Oncology Practice, Jun. 2021, vol. 17, No. 9, pp. e1344-e1353.

Pope et al. "A Retrospective, Multicenter, Quantitative Analysis of Patients' Baseline Pain Quality (PROMIS-29) Entering into Pain and Spine Practices in the United States (ALIGN)," Pain and Therapy, 2021, vol. 10, No. 1, pp. 539-550.

Qaseem et al. "Noninvasive Treatments for Acute, Subacute, and Chronic Low Back Pain: A Clinical Practice Guideline From the American College of Physicians," Annals of Internal Medicine, 2017, vol. 166, No. 7, pp. 514-530.

Rigoard et al. "Multicolumn spinal cord stimulation for predominant back pain in failed back surgery syndrome patients: a multicenter randomized controlled trial," Pain, Jun. 2019, vol. 160, No. 6, 1410-1420.

Rock et al. "Spinal Cord Stimulation," Neurosurgery Clinics of North America, 2019, vol. 30, No. 2, pp. 169-194.

Smith et al. "Effects of present pain level on recall of chronic pain and medication use," Pain, 1993, vol. 55, No. 3, pp. 355-361.

Smith et al. "New technologies, new disparities: The intersection of electronic health and digital health literacy," International Journal of Cardiology, Oct. 2019, vol. 292, pp. 280-282.

Vegesna et al. "Remote Patient Monitoring via Non-Invasive Digital Technologies: A Systematic Review," Telemedicine and e-Health, Jan. 2017, vol. 23, No. 1, pp. 3-17.

Venkatraman et al. "Feasibility study of a novel digital health platform for patients undergoing transcatheter aortic valve replacement," Journal of Cardiac Surgery, 2022, vol. 37, No. 7, pp. 2017-2022.

Venkatraman et al. "Outcomes With a Mobile Digital Health Platform for Patients Undergoing Spine Surgery: Retrospective Analysis," JMIR Perioperative Medicine, 2022, vol. 5, No. 1, article e38690, 12 pages.

Wong et al. "Prevalence, Incidence, and Factors Associated With Non-Specific Chronic Low Back Pain in Community-Dwelling Older Adults Aged 60 Years and Older: A Systematic Review and Meta-Analysis," The Journal of Pain, Apr. 2022, vol. 23, No. 4, pp. 509-534.

Zuidema et al. "Long-term Evaluation of Spinal Cord Stimulation in Patients With Painful Diabetic Polyneuropathy: An Eight-to-Ten-Year Prospective Cohort Study," Neuromodulation: Technology at the Neural Interface, 2023, vol. 26, pp. 1074-1080.

* cited by examiner

Timeline for PROMIS-29 survey responses from Digital Health Platform

Schedule SCSeval

Download CGP Enroll Consent

180

181

183 SCSeval Day

184 SCS Evaluation Period

Baseline Pain Survey PROMIS-29 Survey 182  185 PROMIS-29 Survey

187

Permanent SCS Implant 188-a 188-b 188-c 188-d

4week  6week  8 week  3 month

Preimplant PROMIS-29 Survey

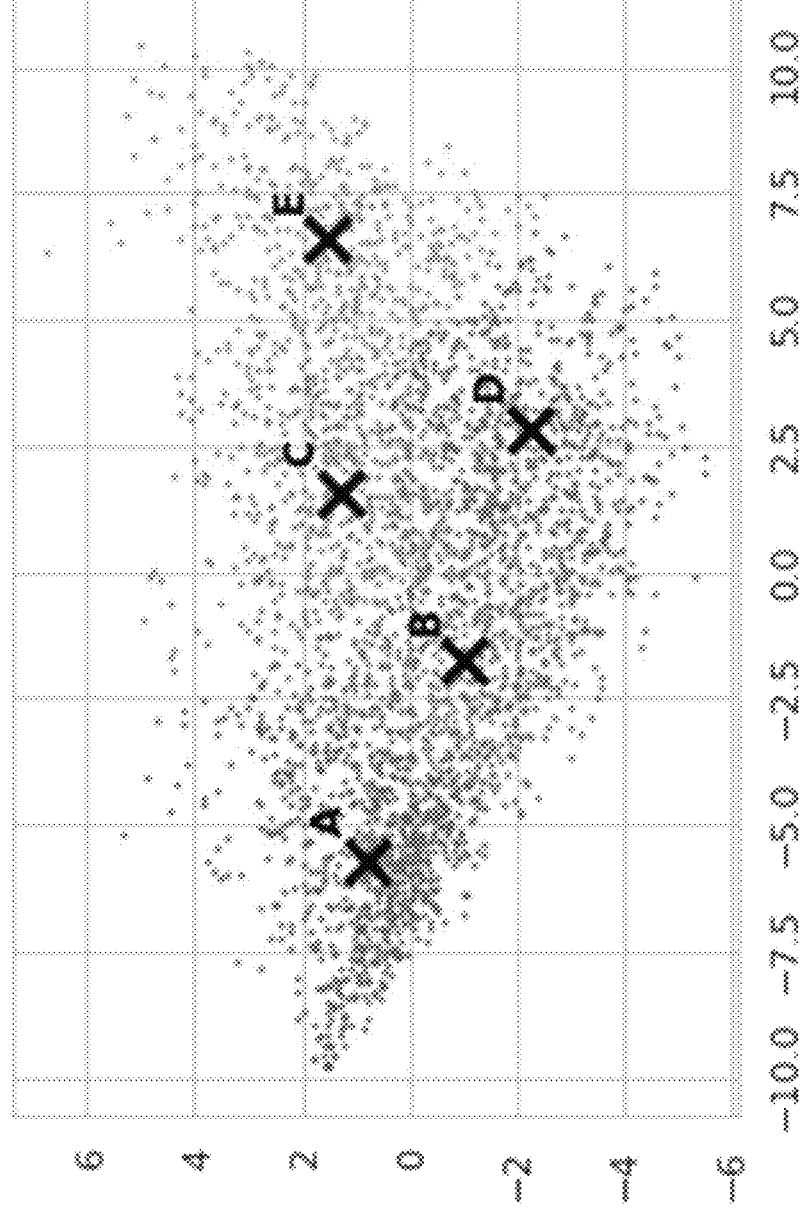
FIG. 8A
Slide 20
800

Slide 20

801

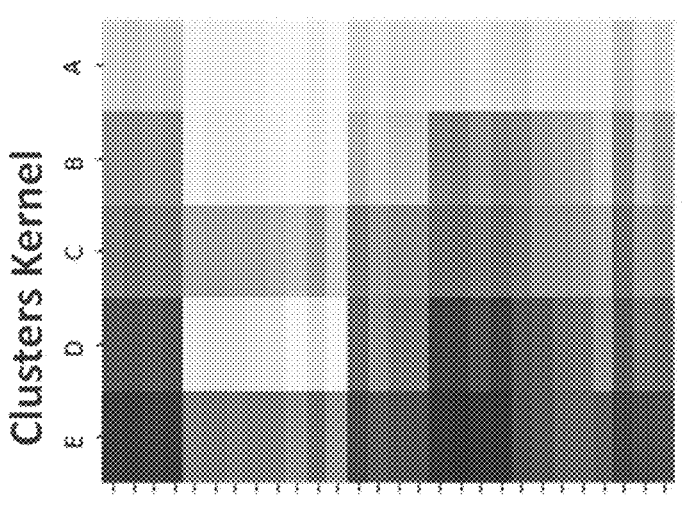
FIG. 8C

1101

1205 — Process Baseline Patient-Provided Answer(s)

1210 — Process Patient-Provided Answer(s)

1215 — Output Notification(s)

1220 — Determine/Confirm Trend

1225 — Determine State(s)

1230 — Determine Rating

1235 — Provide Patient-Provided Answer(s) to Machine Learning Model(s)

1240 — Receive Output

1245 — Generate Metric Data

1250 — Provide Recommendation(s)

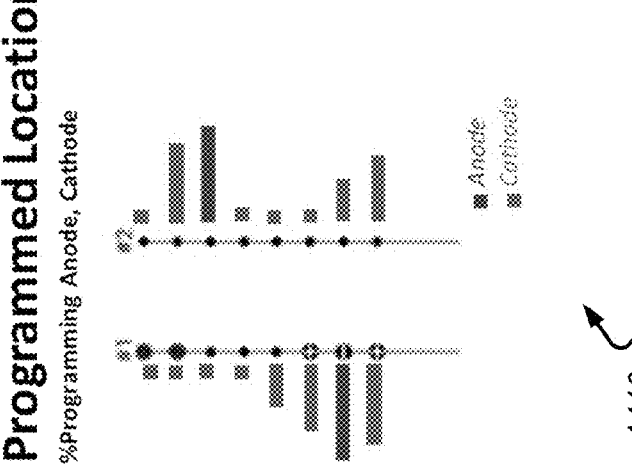
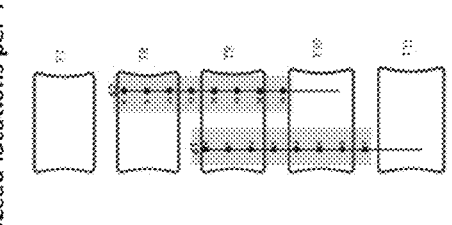
FIG. 14A

| Area | Domain | Responses | Potential associations with Device data |
|---|---|---|---|
| Physical Function | Are you able to do chores such as vacuuming or yard work?<br>Are you able to go up and down stairs at a normal pace?<br>Are you able to go for a walk of at least 15 minutes?<br>Are you able to run errands and shop? | 1. Unable to Do<br>2. With much difficulty<br>3. With some difficulty<br>4. With a little difficulty<br>5. Without any difficulty | 1. Increase % time spent in "Dec" during daytime<br>2. Resting trend (separate from posture information)<br>3. Number transitions in Lying Daytime and NightTime (already available in Australia study) |
| Anxiety | I felt fearful<br>I found it hard to focus on anything other than my anxiety<br>My worries overwhelmed me<br>I felt uneasy | 1. Always<br>2. Often<br>3. Sometimes<br>4. Rarely<br>5. Never | 1. Battery charging behavior (charging too many times (anxious), edge charging (when battery is <5%) indicates risk taking behavior. Charging in a responsible manner (daily at a specific routine), disorganized charging behavior (may indicate depression)<br>2. Stim programming behavior (how often patients change between stim groups)<br>3. Consistency of reprogramming behavior (random or a pattern e.g. Stim group A (awake), Stim group B (sleeping) consistently changed? Randomly? Not changed at all?) |
| Depression | I felt worthless<br>I felt helpless<br>I felt depressed<br>I felt hopeless | | |

FIG. 15A

| Area | Domain | Responses | Potential associations with Device data |
|---|---|---|---|
| Fatigue | I feel fatigued<br>I have trouble starting things because I am tired<br>How run-down did you feel on average?<br>How fatigued were you on average?<br>My sleep was refreshing<br>I had a problem with my sleep<br>I had difficulty falling asleep | 1. Very much<br>2. Quite a bit<br>3. Somewhat<br>4. A little bit<br>5. Not at all | 1. Increase % time spent in Dec at night<br>2. Lower variation in ECAP at night |
| Sleep Disturbance | My sleep quality was | 1. Very poor<br>2. Poor<br>3. Fair<br>4. Good<br>5. Very good | |

FIG. 15B

| Area | Domain | Responses | Potential associations with Device data |
|---|---|---|---|
| Ability to Participate in Social Roles and Activities | I have trouble doing all of my regular leisure activities with others.<br>I have trouble doing all of the family activities that I want to do.<br>I have trouble doing all of my usual work (include work at home).<br>I have trouble doing all of the activities with friends that I want to do. | 1. Always<br>2. Usually<br>3. Sometimes<br>4. Rarely<br>5. Never | 1. Same as "Physical Function"? |
| Pain Interference | How much did pain interfere with your day to day activities?<br>How much did pain interfere with work around the home?<br>How much did pain interfere with your ability to participate in social activities?<br>How much did pain interfere with your household chores? | 1. Very much<br>2. Quite a bit<br>3. Somewhat<br>4. A little bit<br>5. Not at all | 1. Scatter plot of posture or resting status vs. ECAP amplitude may provide some insights |
| Pain Intensity | How would you rate your pain on average? | 0=No pain to 10=Worst imaginable | More consistent therapy dose (associated with ECAP variation)<br>A lower variation of ECAP may be associated with a better and more consistent dose of therapy. |

Determine State(s)

1610

Output Notification

1615

Confirm State(s)

1620

Provide Recommendation(s)

CLINICAL DECISION SUPPORT FOR CHRONIC PAIN MANAGEMENT

CROSS-REFERENCE TO RELATED APPLICATIONS

The present application claims the benefit of and priority to U.S. Provisional Application No. 63/529,344 filed on Jul. 27, 2023, entitled "CLINICAL DECISION SUPPORT FOR CHRONIC PAIN MANAGEMENT", the entirety of which is hereby incorporated herein by reference.

FIELD OF INVENTION

The present disclosure is generally directed to pain management, and relates more particularly to providing recommendations for chronic pain management based on an assessment of multiple domains in a chronic pain patient.

BACKGROUND

Chronic Pain is a difficult condition to treat because, in some cases, treatment may rely on subjective feedback from patients. Techniques are desired which support pain characterization and a nuanced tracking of patient treatment outcomes among those with chronic pain.

BRIEF SUMMARY

Example Aspects of the Present Disclosure Include:

A system including: a processor; and a memory storing instructions thereon that, when executed by the processor, cause the processor to: process one or more inputs including at least one of patient-provided answers and device utilization information in association with at least one health domain, wherein the at least one health domain is associated with one or more chronic conditions; determine one or more states of a patient in association with the at least one health domain based at least in part on processing the one or more inputs; and store information describing the one or more states in an electronic data record.

Any of the aspects herein, wherein determining the one or more states is based on metric information respective to a plurality of health domains including the at least one health domain and where the instructions further enable the processor, when executed, to: provide one or more recommendations associated with the patient based at least in part on the one or more states.

Any of the aspects herein, wherein the one or more states include a characterization of at least one of: an amount of chronic pain of the patient; and a phenotype of the chronic pain.

Any of the aspects herein, wherein the instructions are further executable by the processor to: determine a rating associated with the at least one health domain based at least in part on the one or more patient-provided answers, wherein determining the one or more states of a patient is based at least in part on the rating.

Any of the aspects herein, wherein the instructions are further executable by the processor to: output a notification based at least in part on a trend associated with the one or more states with respect to a temporal period, the notification including at least one of: a request for the patient to provide one or more additional patient-provided answers; and a request for medical personnel to provide input; and determine a rating associated with the at least one health domain based on processing the one or more additional patient-provided answers, the input, or both.

Any of the aspects herein, wherein the instructions are further executable by the processor to: provide the one or more inputs to one or more machine learning models; and receive an output from the one or more machine learning models in response to the one or more machine learning models processing the one or more inputs, wherein the output includes the one or more states, the one or more recommendations, profile information associated with the patient, or a combination thereof.

Any of the aspects herein, wherein the instructions are further executable by the processor to: train a plurality of machine learning models based at least in part on a training data set associated with a plurality of reference patients, wherein the training data set includes a reference set of patient-provided answers in association with the at least one health domain; and define threshold values corresponding to a set of candidate states based at least in part on the training, wherein the one or more states are determined from among the set of candidate states, wherein determining the one or more states, providing the one or more recommendations, or both is based at least in part on one or more machine learning models included in the plurality of machine learning models correlating the one or more patient-provided answers to the one or more states based at least in part on the threshold values.

Any of the aspects herein, wherein: the one or more patient-provided answers and the one or more states are associated with first temporal information; and the instructions are further executable by the processor to: determine a trend associated with the one or more states and the one or more additional states, wherein determining the trend includes: processing one or more second inputs including at least one of patient-provided answers and second device utilization information in association with the at least one health domain and second temporal information; and determining the one or more second states based at least in part on processing the one or more inputs, wherein providing the one or more recommendations is based at least in part on determining the trend.

Any of the aspects herein, wherein the instructions are further executable by the processor to: generate a graphical chart including a visualization of a set of states in association with a set of health domains, wherein the set of health domains includes the at least one health domain and the set of states includes the one or more states.

Any of the aspects herein, wherein: each of the one or more states is determined in association with a plurality of health domains including the at least one health domain.

Any of the aspects herein, wherein the one or more recommendations are associated with at least one of: one or more behaviors of the patient; posture information associated with the patient; one or more medications associated with the patient; one or more device settings associated with delivering therapy to the patient; the device utilization information; and imaging data including location data of one or more device components for delivering the therapy to the patient.

Any of the aspects herein, wherein the instructions are further executable by the processor to: process one or more baseline patient-provided answers included in a baseline pain history survey associated with the patient, wherein determining the one or more states, providing the one or more recommendations, or both is based at least in part on processing the one or more baseline patient-provided answers.

Any of the aspects herein, wherein the instructions are further executable by the processor to at least one of: generate patient level metric data associated with the one or more states and the at least one health domain with respect to the patient; and generate population level metric data associated with the one or more states and the at least one health domain with respect to a plurality of patients, the plurality of patients including at least the patient, wherein providing the one or more recommendations is based at least in part on the patient level metric data, the population level metric data, or both.

Any of the aspects herein, wherein the one or more recommendations are associated with delivering therapy to the patient, the therapy including a neuromodulation therapy.

Any of the aspects herein, wherein the therapy includes spinal cord stimulation.

Any of the aspects herein, wherein the therapy includes peripheral nerve stimulation.

A method including: processing one or more inputs including at least one of patient-provided answers and device utilization information in association with at least one health domain, wherein the at least one health domain is associated with one or more chronic conditions; determining one or more states of a patient in association with the at least one health domain based at least in part on processing the one or more inputs; and storing information describing the one or more states in an electronic data record.

Any of the aspects herein, wherein the one or more states indicate an amount of chronic pain of the patient in association with the at least one health domain and the method further includes providing one or more recommendations associated with the patient based at least in part on the one or more states.

Any of the aspects herein, further including: generating profile information associated with the patient, the profile information including an indication of the one or more states, wherein providing the one or more recommendations is based at least in part on the profile information.

A non-transitory computer readable medium including instructions, which when executed by a processor: process one or more inputs including at least one of patient-provided answers and device utilization information in association with at least one health domain, wherein the at least one health domain is associated with one or more chronic conditions; determine one or more states of a patient in association with the at least one health domain based at least in part on processing the one or more inputs; and store information describing the one or more states in an electronic data record.

A system including: a processor; and a memory storing instructions thereon that, when executed by the processor, cause the processor to: determine one or more states of a patient based at least in part on processing: one or more patient-provided answers associated with at least one health domain; and data from one or more devices associated with providing treatment to the patient or monitoring the patient; and provide one or more recommendations associated with the patient based at least in part on the one or more states.

Any of the aspects herein, wherein the one or more recommendations include one or more recommended patient behaviors.

Any of the aspects herein, wherein the one or more recommendations include one or more recommended operational parameters associated with the one or more devices.

Any of the aspects herein, wherein the one or more recommendations include one or more recommended device parameters associated with delivering therapy to the patient.

Any of the aspects herein, wherein the one or more states include a mental state, a physical state, or both.

Any of the aspects herein, wherein the one or more devices include a therapy device providing therapy to the patient, and the data includes one or more stimulation parameters associated with providing the therapy to the patient.

Any of the aspects herein, wherein the one or more devices include a therapy device providing therapy to the patient, and the data includes at least one of: battery charging activity associated with the therapy device; programming activity associated with the therapy device; and reprogramming activity associated with the therapy device.

Any of the aspects herein, wherein: the one or more devices include a therapy device providing stimulation to the patient; and the data includes an amplitude, a variation in the amplitude, or both of a data signal received by the therapy device, wherein the data signal includes an evoked compound action potential (ECAP) signal, an evoked compound muscle action potential (ECMAP) signal, or both.

Any of the aspects herein, wherein the one or more devices include a wearable device, and the data includes at least one of: physiological data of the patient; motion data associated with the patient; and posture data associated with the patient.

Any of the aspects herein, wherein the one or more devices include an implanted stimulation device.

Any of the aspects herein, wherein the one or more states are determined in association with: the at least one health domain; at least one second health domain different from the at least one health domain; or a combination thereof.

Any of the aspects herein, wherein the one or more recommendations are provided in association with: the at least one health domain; at least one second health domain different from the at least one health domain; or a combination thereof.

Any of the aspects herein, wherein the one or more states are determined based at least in part on an association between the one or more patient-provided answers, the data from the one or more devices, and the one or more states.

Any of the aspects herein, wherein the instructions are further executable by the processor to: output a notification based at least in part processing the one or more patient-provided answers, the notification including a request for the patient to provide one or more second patient-provided answers associated with the at least one health domain, at least one second health domain, or both; and confirming the one or more states based at least in part on processing the one or more second patient-provided answers.

Any of the aspects herein, wherein the one or more patient-provided answers include one or more patient reported outcomes associated with a predefined survey.

Any of the aspects herein, wherein determining the one or more states is based at least in part on determining one or more trends associated with the data with respect to a temporal period.

A method including: determining one or more states of a patient based at least in part on processing: one or more patient-provided answers associated with at least one health domain; and data from one or more devices associated with providing treatment to the patient or monitoring the patient; and providing one or more recommendations associated with the patient based at least in part on the one or more states.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/implementations in combination with any one or more other aspects/features/implementations.

Use of any one or more of the aspects or features as disclosed herein.

It is to be appreciated that any feature described herein can be claimed in combination with any other feature(s) as described herein, regardless of whether the features come from the same described implementation.

The details of one or more aspects of the disclosure are set forth in the accompanying drawings and the description below. Other features, objects, and advantages of the techniques described in this disclosure will be apparent from the description and drawings, and from the claims.

The preceding is a simplified summary of the disclosure to provide an understanding of some aspects of the disclosure. This summary is neither an extensive nor exhaustive overview of the disclosure and its various aspects, implementations, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, implementations, and configurations of the disclosure are possible utilizing, alone or in combination, one or more of the features set forth above or described in detail below.

Numerous additional features and advantages of the present disclosure will become apparent to those skilled in the art upon consideration of the implementation descriptions provided hereinbelow.

BRIEF DESCRIPTION OF THE SEVERAL
VIEWS OF THE DRAWINGS

The patent or application file contains at least one drawing executed in color. Copies of this patent or patent application publication with color drawing(s) will be provided by the Office upon request and payment of the necessary fee.

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, implementations, and configurations of the disclosure, as illustrated by the drawings referenced below.

FIG. 3 illustrates example clusters of chronic pain characteristics which may be determined using hierarchical clustering in accordance with aspects of the present disclosure.

FIG. 8A includes an example plot illustrative of clustering based on baseline data and end of trial data to generate multipole states in accordance with aspects of the present disclosure.

Figure 8B:
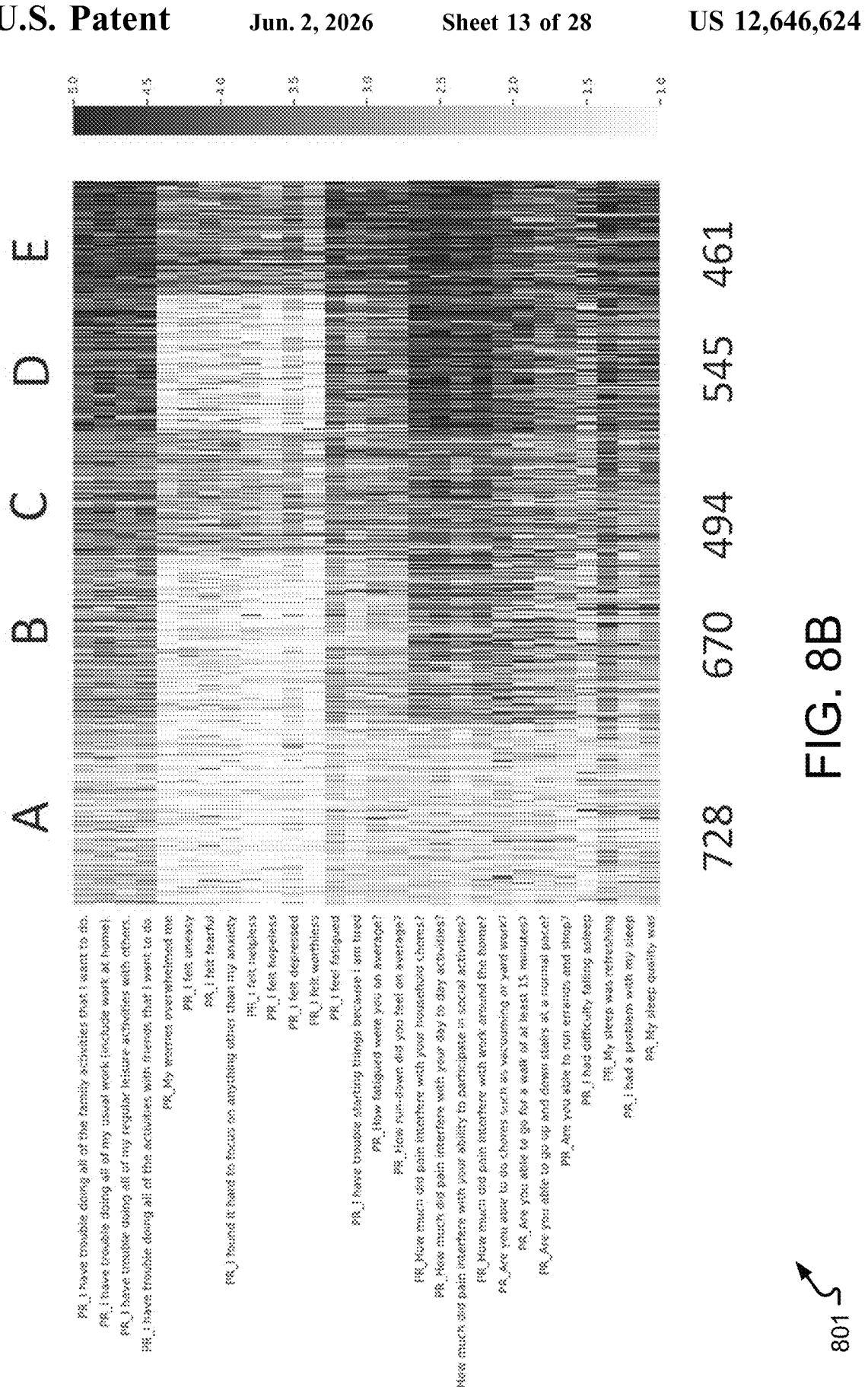

FIG. 8B includes an example plot illustrative of individual PROMIS-29 question responses.

FIG. 8C includes an example plot illustrative of kernel clustering of pain states A through E in accordance with aspects of the present disclosure.

Figure 9A:
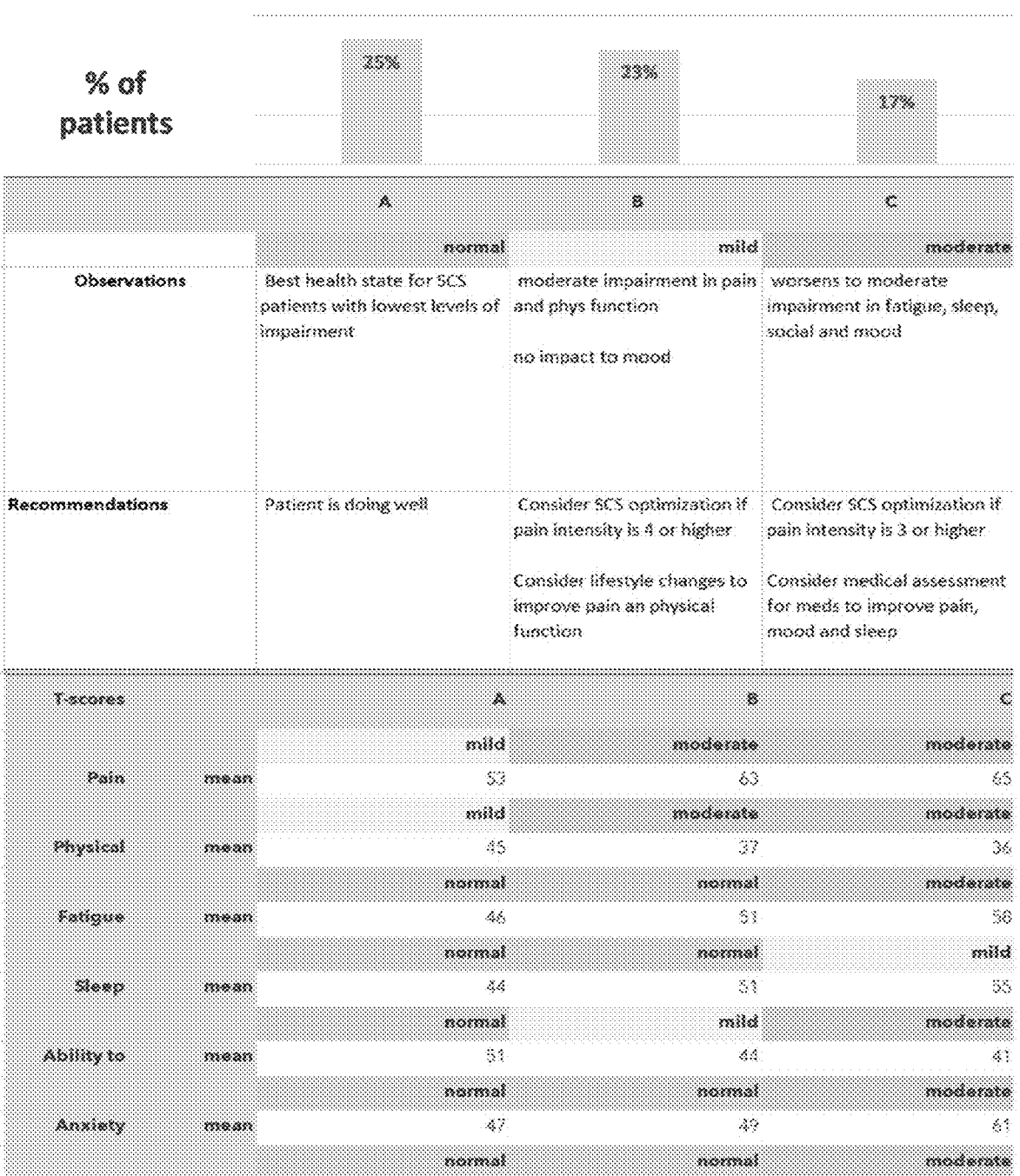
Figure 9B:
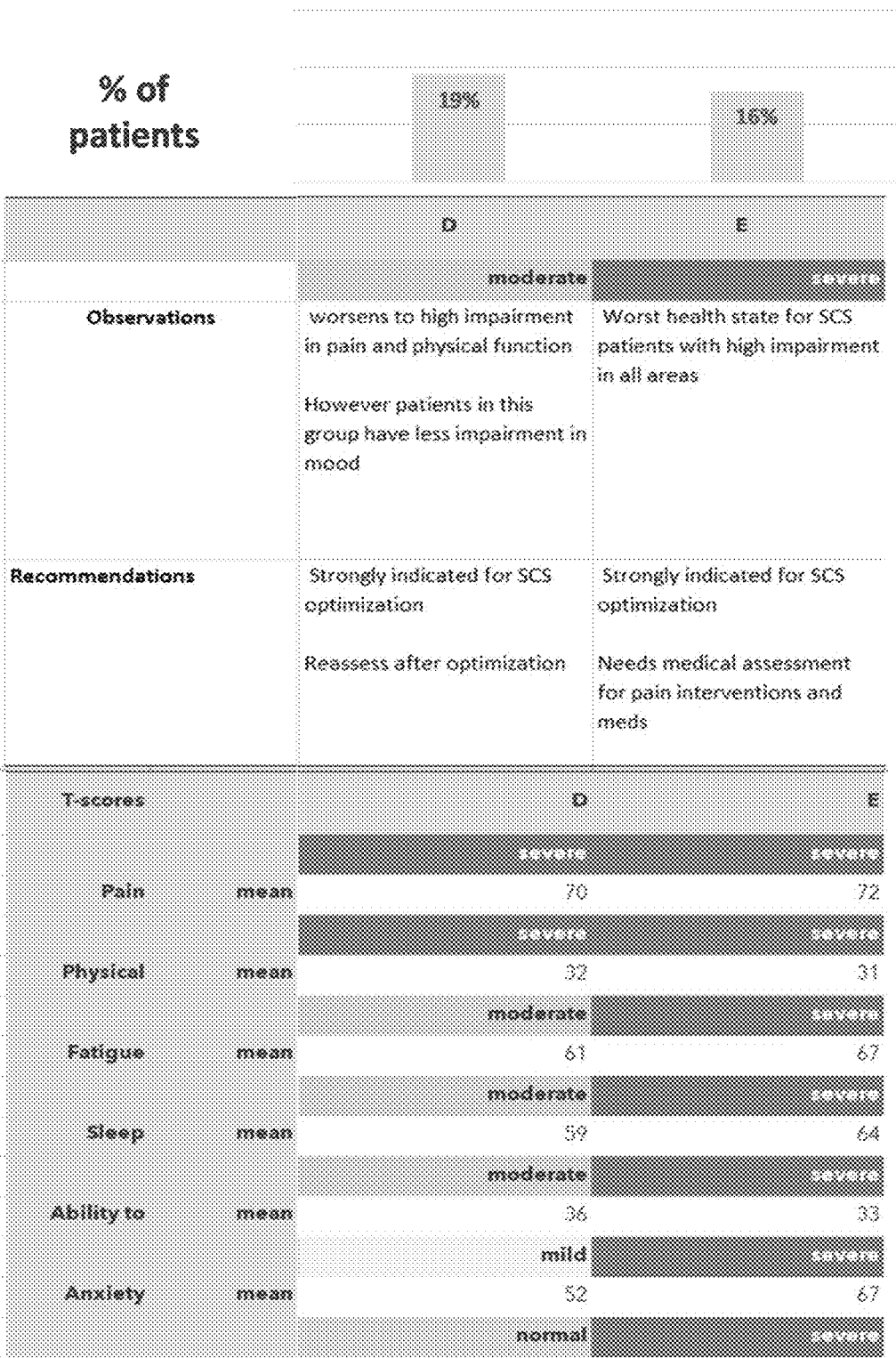

FIGS. 9A and 9B illustrate example aspects of preliminary clinical decision interpretation for pain states in accordance with aspects of the present disclosure.

Figure 10:
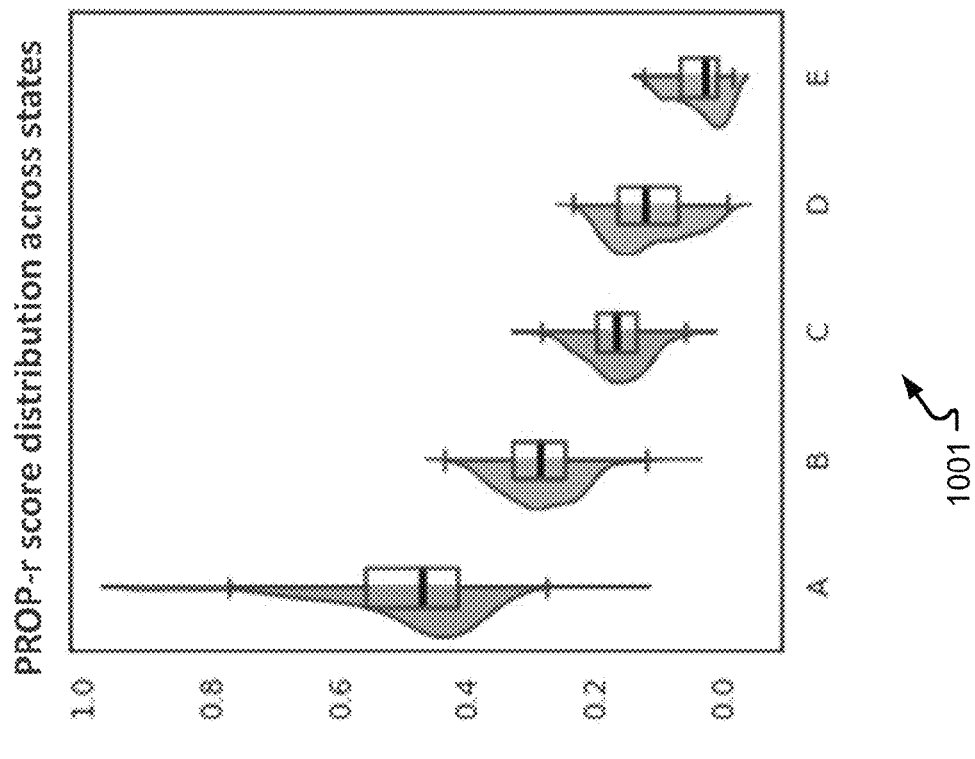

FIG. 10 illustrates an example of corroboration of state severity and pain intensity (PROPr) supported by aspects of the present disclosure.

Figure 11A:
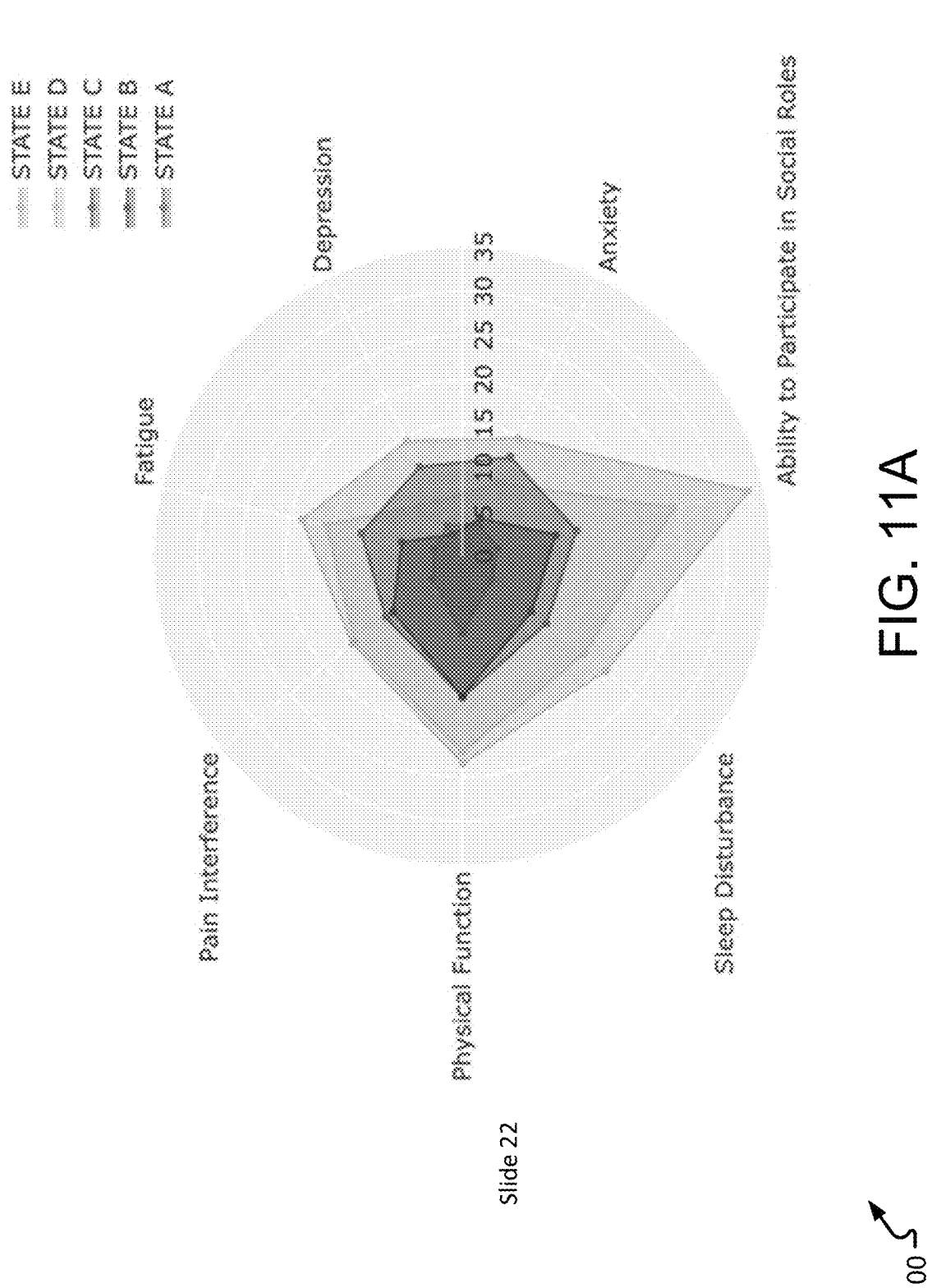
Figure 11B:
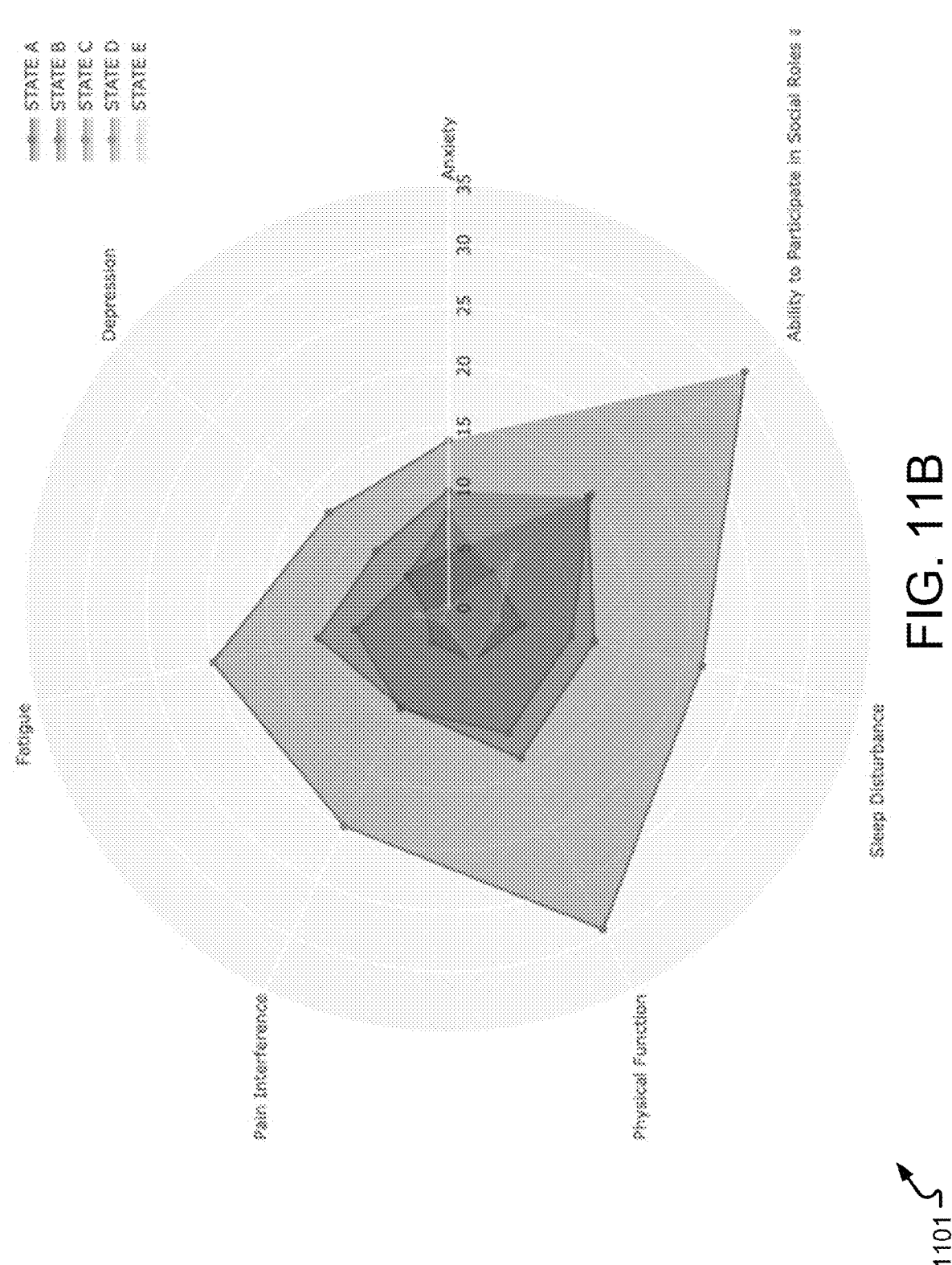

FIGS. 11A and 11B illustrate example radar plots supported by aspects of the present disclosure.

Figure 12:
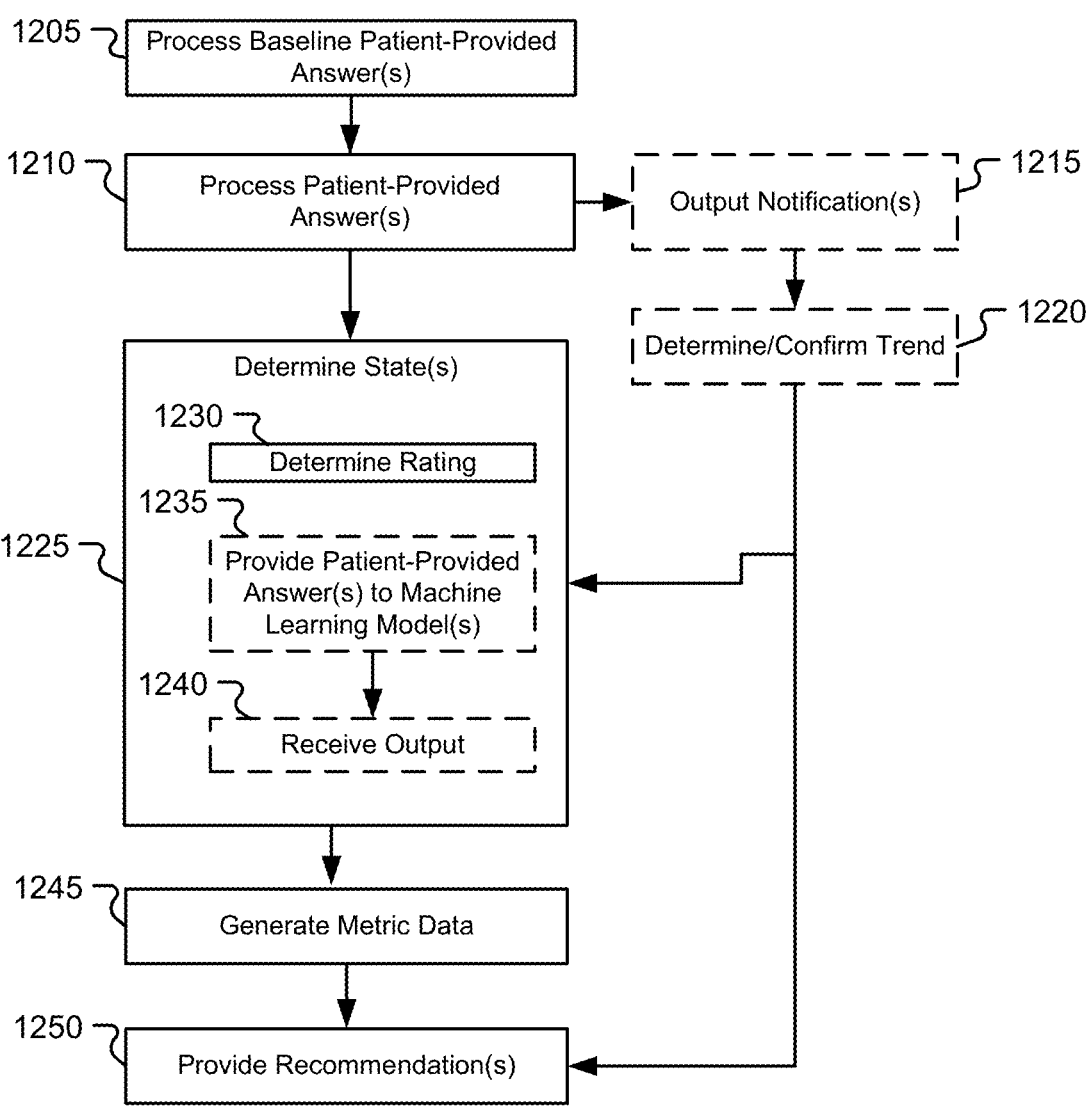

FIG. 12 illustrates an example of a process flow in accordance with aspects of the present disclosure.

Figure 13:
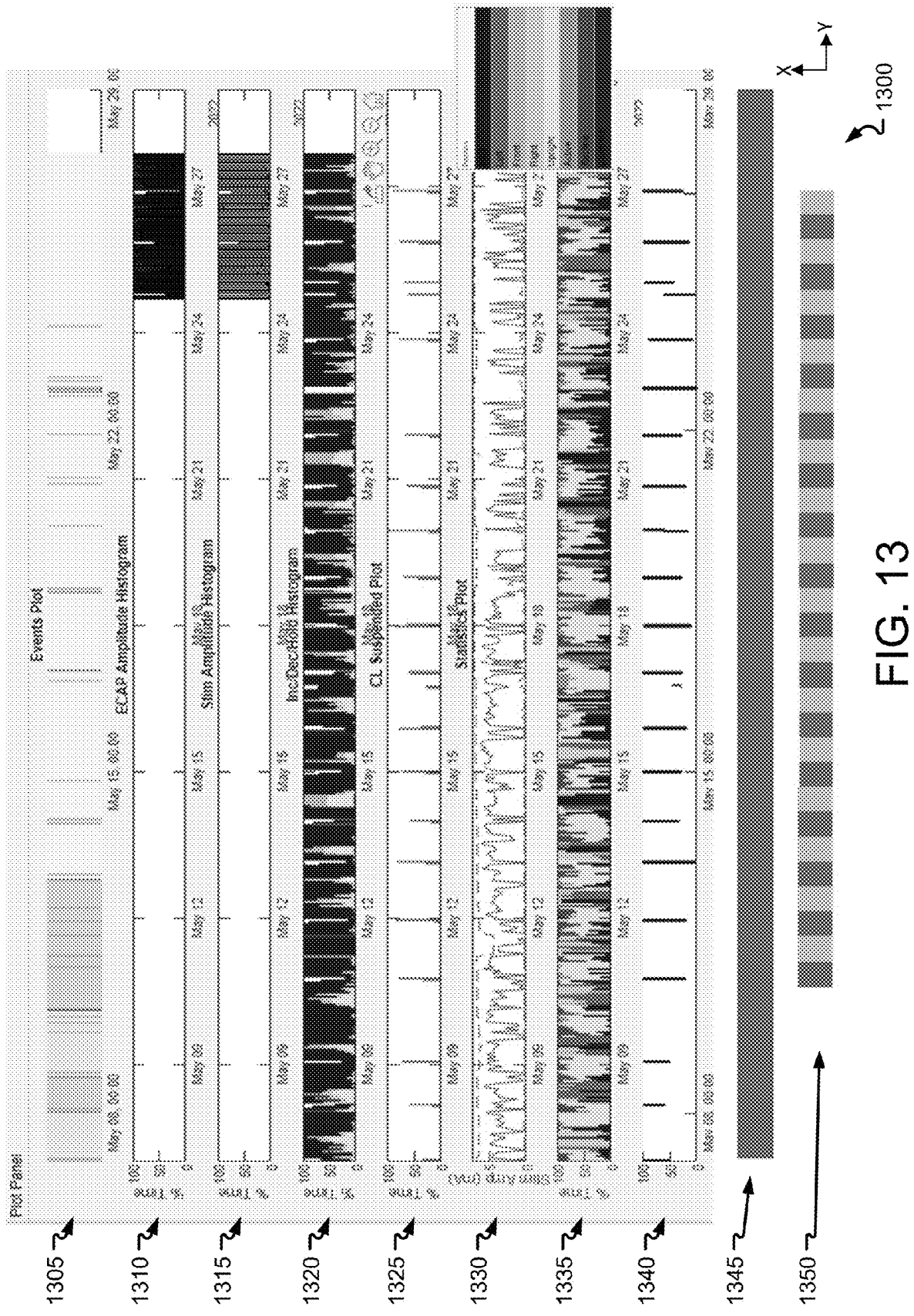

FIG. 13 illustrates a timeline including examples of device data in accordance with aspects of the present disclosure.

Figure 14B:
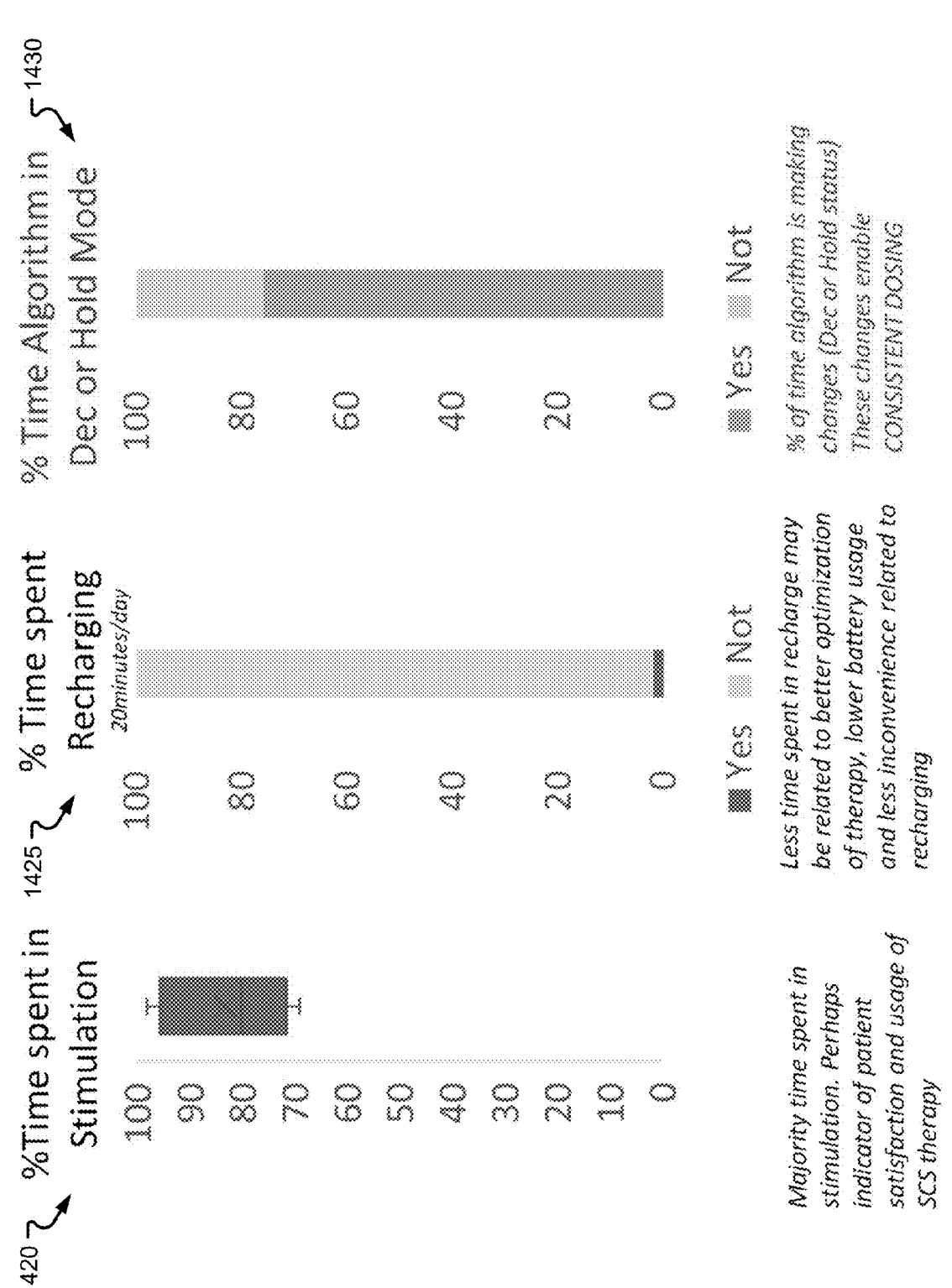
Figure 14C:
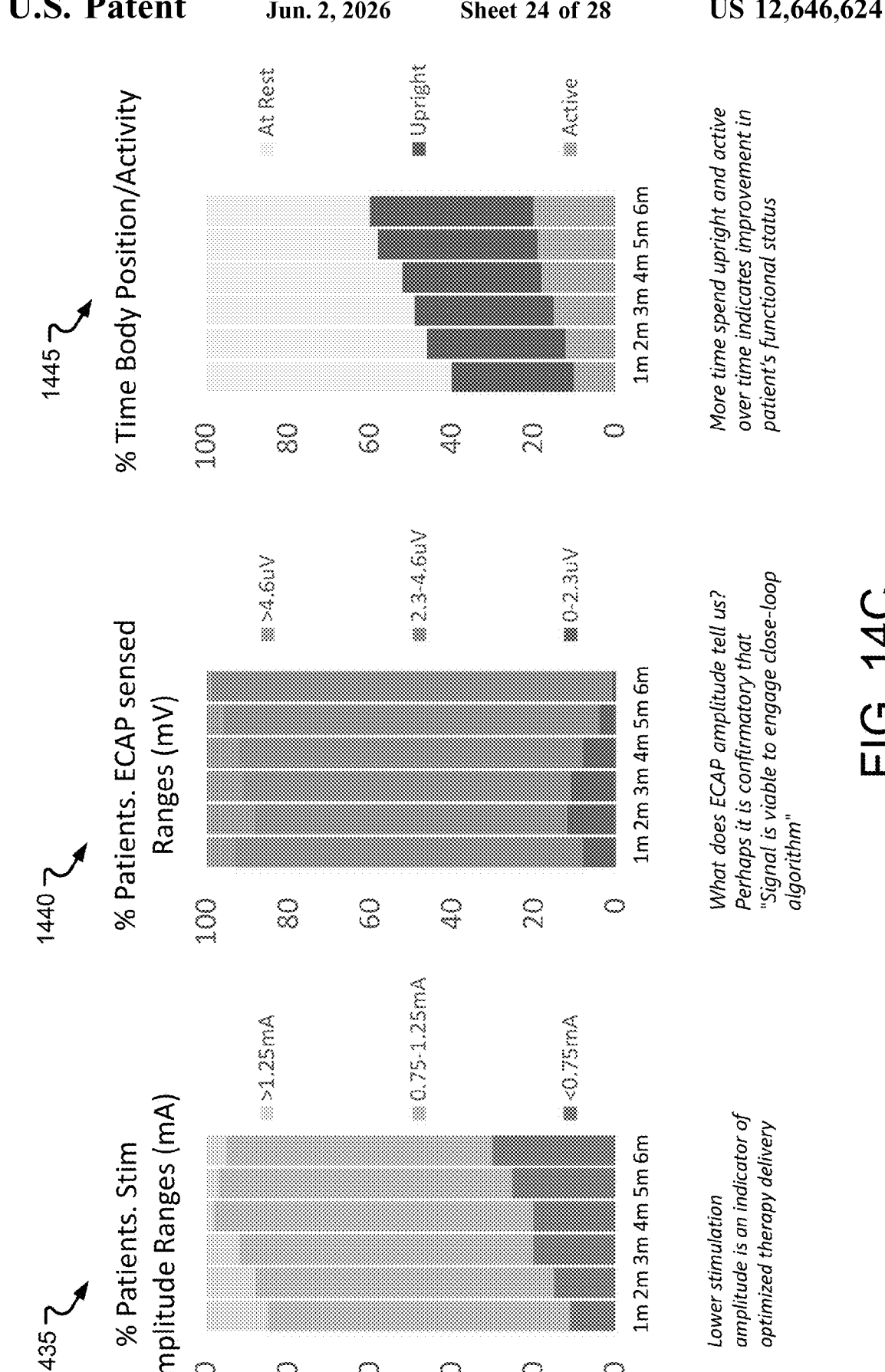

FIGS. 14A through 14C illustrate examples of clinical metrics derivable from device data described herein in accordance with aspects of the present disclosure.

FIGS. 15A through 15C illustrate example associations between device based metrics and standard survey domains, supportive of determining objective measures of chronic pain from an implantable medical device and/or a wearable device in accordance with aspects of the present disclosure.

Figure 16:
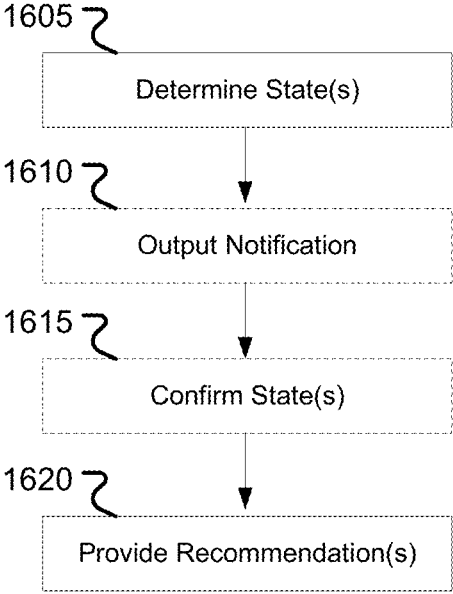

FIG. 16 illustrates an example of a process flow in accordance with aspects of the present disclosure.

DETAILED DESCRIPTION

It should be understood that various aspects disclosed herein may be combined in different combinations than the combinations specifically presented in the description and accompanying drawings. It should also be understood that, depending on the example or implementation, certain acts or events of any of the processes or methods described herein may be performed in a different sequence, and/or may be added, merged, or left out altogether (e.g., all described acts or events may not be necessary to carry out the disclosed techniques according to different implementations of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10× Fusion processors; Apple A11, A12, A12X, A12Z, or A13 Bionic processors; or any other general purpose microprocessors), graphics processing units (e.g., Nvidia Geforce RTX 2000-series processors, Nvidia Geforce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any implementations of the disclosure are explained in detail, it is to be understood that the disclosure is not limited in its application to the details of construction and the arrangement of components set forth in the following description or illustrated in the drawings. The disclosure is capable of other implementations and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Chronic Pain is a difficult condition to treat because, in some cases, treatment may rely on subjective feedback from patients. For some acute illnesses (e.g., flu) experienced by the patients, developed diagnostics enable clinicians to promptly diagnose the condition based on a combination of history, physical and diagnostic biomarkers, and accordingly, treat the patient. For some chronic diseases (e.g., diabetes, heart failure, etc.) established biomarkers (e.g., blood glucose, BNP respectively) are available that enable accurate and timely diagnosis via the biomarkers and diagnostics (e.g., echo cardiogram).

Diagnosis of chronic pain severity, however, is not obvious in most instances. For example, some techniques for diagnosis of chronic pain severity are based on subjective data (e.g., patient reported symptoms and feelings), and patient reporting of the subjective data may be influenced by concomitant mental and functional factors. In some cases, when a patient receives therapy for chronic pain, the measurement of improvement thereafter (e.g., as reported by the patient) may be again influenced by the same subjective measures.

Aspects of the present disclosure support techniques of accurately determining a state of a patient, determining changes in patient states, and/or providing recommendations for chronic pain management based on data analytics (e.g., based on determining the state of the patient or changes in patient states). For example, the systems and techniques described herein support generating an accurate assessment of multiple domains in a chronic pain patient and providing recommendations for chronic pain management based on the assessment. The systems and techniques support collecting information about the health status of a patient from multiple domains and putting the collected information into the context of the therapy options for the patient, which may support improved treatment outcomes and optimized remote monitoring of patients.

Examples of a clinical decision support tool and a framework supportive of the systems and techniques of the present disclosure are described herein. In an example, the clinical decision support tool and framework include a digital health platform application (e.g., on a patient's phone, a browser of a computing device, etc.) that may prompt a patient, at one or more determined time intervals (e.g., predetermined time intervals), to respond to survey questions. The digital health platform application may be a patient-centric, educational healthcare application capable of supporting patients on a therapy journey (e.g., a spinal cord stimulation (SCS) journey, etc.). For example, the digital health platform application may provide insights on real-world data associated with a patient and long-term treatment outcomes. In some non-limiting examples, the digital health platform application may be any suitable digital health platform application supportive of the techniques described herein. In some aspects, the host for the digital health platform may be a portable computing device (e.g., a patient's phone), another computing device, a web portal, and the like.

The survey questions may be based on a standardized measure of quantifying the mental and physical status of a patient. For example, the survey questions posed to the patient may be provided in association with a set of person-centered measures (e.g., PROMIS® (Patient-Reported Outcomes Measurement Information System®)) that evaluates and monitors physical, mental, and social health patients. In some aspects, the survey questions may be based on a standard instrument PROMIS-29 that quantifies the mental and/or physical status of a patient in multiple domains and quantifies pain intensity. In an example implementation, the survey questions may quantify the mental and physical status of a patient in 7 domains (e.g., with four questions each, where each question has a potential for one of five responses) and quantify pain intensity. Various example aspects of the digital health platform application, the survey questions, and response options with respect to the present disclosure are described in the Exhibits provided with the present application.

In some aspects, based on responses to one or more of the survey questions (e.g., each of the survey questions), an amount that a device is used by the patient, or combinations thereof, the techniques described herein include placing a patient into one of multiple candidate domains that predefine the chronic pain state of a patient. In an example, the techniques described herein include placing a patient into one of five states (e.g., A, B, C, D, E) that predefine the chronic pain state of a patient. In an example, state A through state E may indicate relatively increasing amounts of severity of chronic pain. For example, state A may indicate the least severity and state E may represent the highest severity of chronic pain. In addition to determining the state associated with a patient, information describing the state may be stored in an electronic data record associated with the patient (e.g., for future reference, for analysis by a care provider, for determining a pain interference score, for generating a recommendation, etc.).

The systems and techniques may support defining the states A through E using machine learning techniques. For example, the techniques described herein may support training of machine learning models capable of processing one or more inputs, which may include responses of a patient to survey questions, device utilization (e.g., how frequently a device is used by the patient, how frequently a therapy is provided from the device to the patient, how frequently the patient responds to survey questions, etc), and determining, based on processing the responses, the states of the patient. In an example implementation, the techniques described herein include defining the states based on unsupervised learning from reference patient data (e.g., patient data of 1600 more patients).

According to example aspects of the present disclosure, the systems and techniques include utilizing the states to understand the status (e.g., health status) of a patient and direct therapy delivery. In some aspects, as data is received on the digital health platform, the digital health platform may determine one or more current states of the patient. In an example, each 'state' is a discrete representation of the health status a patient in relation to pain and one or more quality of life domains. Other example aspects of the states are later described herein.

The systems and techniques described herein support observing trends in states (e.g., improvement, worsening, remaining the same). For example, the digital health platform may support generating reports indicating the states and respective trends. In an example, the systems and techniques described herein include providing, based on the trends, decisions (e.g., clinical decisions, etc.) and identified areas for improvement (e.g., identified health domains for improvement). In some examples, the clinical decisions may be associated with behavioral changes, medication changes, device programming, other treatment recommendations, and the like. Trends can also be utilized to identify which patient(s) are likely to benefit from an optimization to their therapy. For instance, based on a pain state or a trend of a patient's pain state, embodiments of the present disclosure contemplate a clinical recommendation engine that is capable of moving a patient from one state to another state by adjusting (e.g., optimizing) the patient's therapy (e.g., by way of providing physical therapy recommendations, medication recommendations, mood treatment recommendations, stimulation therapy recommendations, etc.).

Aspects of the techniques described herein may support therapy related to pain stimulation. For example, the therapy may include a neuromodulation therapy. In some example implementations, the therapy may include spinal cord stimulation (SCS), drug delivery (e.g., intrathecal drug delivery (TDD)), deep brain stimulation (DBS), and pelvic health stimulation, but is not limited thereto.

As described herein, the systems and techniques enable optimized care of chronic pain patients, enable remote care of patients (e.g., based on determined states and respective trends), and provide improved management of therapy devices allocated to patients (e.g., management of device programming, etc.). The systems and techniques provide patient analytics which may be implemented in a clinical decision support tool, example aspects of which are described herein.

Implementations of the present disclosure provide technical solutions to one or more of the problems of providing a quantified representation of the health status of a patient in relation to pain and other quality of life domains. For example, though domains may be used as different aspects of quality of life in a PROMIS-29 questionnaire, the information in the PROMIS-29 questionnaire is absent a discrete representation (e.g., 'states' described herein) of the health status of the patient in relation to pain and other quality of domains. In some aspects, providing quantified representations (e.g., 'states') of the health status of a patient may support effective characterization of chronic pain, increased success rates associated with treatment plans, and increased success rates associated with therapy delivery devices (e.g., medical implants).

According to other example aspects of the present disclosure, the systems and techniques described herein may support determining objective measures of chronic pain from an implantable medical device and/or a wearable device.

Some approaches to characterize chronic pain include simply asking the patient about their pain on a scale (0-10 or 0-100) over a temporal period (e.g., a 24 hour period, a 72 hour period, and the like). Such subjective measures are then also used to determine patient response to temporary SCS and permanent SCS usage. In some cases, the implanting physician defines a successful evaluation as a 50% or higher reduction in pain or an improvement in quality of life. Example aspects of temporary SCS and a corresponding trial period that support aspects of the present disclosure are later described herein. Chronic pain may additionally or alternatively be characterized based on a patient's utilization of a device. Utilization of a therapy delivery device less frequently may provide an indication of an improvement in patient state. Such inputs (e.g., patient responses and/or device utilization information) may be provided to one or more neural networks for purposes of determining the patient state or a recommendation for the patient.

SCS is a proven therapy option for patients for whom other medical and surgical therapies are not providing adequate pain relief. Stimulator leads are guided into the epidural space and attached to an implanted pulse generator that provides electrical stimulation to the dorsal horns of the spinal cord, interrupting pain signals. Clinical trials have proven the efficacy of SCS in chronic lower back and leg pain, failed-back-surgery syndrome, complex regional pain syndrome, and painful diabetic neuropathy.

Since chronic pain experiences are complex and unique to each patient, and affect numerous facets of their life, techniques are desired that support objectively quantifying chronic pain using implantable medical device/wearable data, which may provide examples of device utilization information. Systems and techniques are described herein which, using an association of (relevant) metrics retrieved from an implantable medical device/wearable device with standard tools (e.g., PROMIS-29 survey), provide a mechanism to quantify meaningful metrics associated with chronic pain.

In some aspects, the systems and techniques described herein support providing quantifiable measures of chronic pain. The systems and techniques may utilize the quantifiable measures to monitor chronic pain patients and to monitor the effectiveness of SCS in device recipients. In some examples, utilizing the quantifiable measures may enable direct association of SCS therapy and outcome.

An Example Framework of the Objective Quantification is as Follows:

Baseline data. The baseline data may include pre-SCS information provided by a wearable device or from a baseline survey. In some cases, the pre-SCS information may include patient demographics, disease states, comorbidities and/or risk factors (e.g., smoking, etc.)).

Imaging information. In some aspects, the imaging information may be noted in device data.

Patient reported outcome (e.g., Pain Intensity, seven domains of PROMIS-29) are collected using a digital health platform. The digital health platform may reside on a patient's device (e.g., mobile device, mobile phone, smartwatch, etc.) and prompt the patient, at pre-determined time intervals, to respond to survey questions. The digital health platform is an app based decentralized clinical trial (DCT) tool that enables survey data collection from patients to be evaluated (e.g., chronic pain patients with SCS implants).

The specific questions that are posed to the patient may be based on a standard methodology (e.g., PROMIS-29) as described herein.

SCS device data (and/or wearable device data) is retrieved at an in-clinic follow-up. The follow-up may be a scheduled or unscheduled follow-up after permanent SCS implant.

Derive clinical metrics and trends from the device data.

Providing, based on an association of patient reported outcome (PRO) and device metrics, a quantification of patient's chronic pain status.

Using the objective measures to manage the patient, for example, in relation to neuromodulation therapy (e.g., spinal cord stimulation (SCS)), drug delivery (e.g., intrathecal drug delivery (TDD)), device programming, and the like.

It is to be understood that the framework of the objective quantification is not limited to the examples described herein, and the systems and techniques described herein support a framework including any suitable combination of the examples.

The objective quantification of chronic pain, as provided by the systems and techniques described herein, relate to data analytics and insights from the data, resulting in a potential for quantifying a patient's condition. The quantifications provided herein would enable physicians to provide improved management of patients.

The objective quantification of chronic pain, as provided by the systems and techniques described herein, may provide definitive proof of positive benefit of SCS in chronic pain recipients. The objective quantifications described herein may support increased adoption of SCS therapy. In some other aspects, the objective quantifications may enable improved clinical decision support so that the SCS therapy can be optimized in patients.

According to example aspects of the present disclosure, systems and techniques are described herein with respect to a digital health platform supportive of patients undergoing spinal cord stimulation evaluations. It is to be understood that the systems and techniques may be extended to other therapy techniques (e.g., other neuromodulation therapy, drug therapy, etc.).

Spinal cord stimulation (SCS) is an effective treatment for those experiencing chronic back and leg pain. SCS involves a temporary evaluation period (SCSeval, also referred to herein as SCSeval period, an SCS trial, or evaluation period) before permanent implantation of a therapy device. A mobile digital health platform described herein may support providing education, feedback, and collected outcomes during a surgical journey of a patient undergoing SCSeval. Systems and techniques associated with the digital health platform may support the analysis of preoperative patient demographics, characterization of patient pain profiles using PROMIS-29 surveys, and the calculation of the rates of conversion from temporary to permanent SCS implantation.

Example aspects of the systems and techniques described herein support utilizing a mobile application associated with the digital health platform for treating patients experiencing pain symptoms (e.g., aching, sharp, stabbing, tingling, numb, and burning pain). The systems and techniques described herein provide advantages in determining therapy settings and treatments for patients for which other therapies are unsuccessful and/or who wish to reduce their use of opioids and pain medications.

Aspects of the systems and techniques may provide significant improvement in all domains of pain as evaluated by pre-and-postoperative PROMIS-29 surveys. The systems and techniques described herein support the use of digital health technology as part of the SCS journey to improve the patient experience and allow for robust patient reported outcomes collection. In some aspects, the systems and techniques provide an overall rate of SCSeval to permanent SCS of 72.4%, which is higher than national rates of 64%.

Aspects of the digital health platform application described herein may enable clinicians to quantify changes in chronic pain. Features of the digital health platform application may provide insight into choosing to implant SCS permanently. The tools described herein provide for effective pain characterization and allow for more nuanced tracking of patient outcomes among those with chronic pain. In particular, but without limitation, a pain flag may be utilized to characterize a current pain state, a change in pain state, or some other indication of a patient's trend in state. For instance, a pain flag representing a current or dynamically-changing pain state may indicate whether an update to the SCS therapy is desired.

It is estimated that 20.4% of US adults (50 million) suffer from chronic pain, with 8% of US adults (19.6 million) experiencing severe chronic pain that substantially interferes with their daily lives. Additionally, chronic pain contributes to an estimated $560 billion each year in direct medical costs, lost productivity and disability programs. SCS is a proven therapy option for these patients where other medical and surgical therapies are not providing adequate pain relief.

Clinical trials have proven the efficacy of SCS in chronic lower back and leg pain, failed-back-surgery syndrome, complex regional pain syndrome, and painful diabetic neuropathy. Using a temporary SCS device (also referred to herein as a trial device), patients can assess the efficacy of SCS therapy during a 3-10 day evaluation in which clinicians closely observe their patients and monitor their pain levels. In some cases, the implanting physician defines a successful evaluation as a 50% or higher reduction in pain or an improvement in quality of life. A patient is eligible for a permanent SCS implant if other treatment modalities (e.g., medication, surgery, physical therapy, psychological therapy) have failed, the patient has undergone physical and psychological evaluation, and the patient has completed a successful SCS temporary evaluation (SCSeval).

The temporary SCS device may include various programming information. In some cases, the programming information may include multiple programs, and the multiple programs (e.g., usage of the various programs) may be tied to various respective patient outcomes. In some example implementations, the temporary SCS device may include an accelerometer and/or provide ECAP data and/or provide imaging data.

In some cases, the patient may have had multiple programs, and ML algorithms supported by aspects of the present disclosure may include information on therapy relief for different settings of the temporary SCS device. For example, in some cases, patients may be programmed with 3 groups, and the temporary SCS device may support switching between groups or changing amplitudes to achieve a target outcome (e.g., the patient may gain adequate pain relief). The systems and techniques described herein may combine the programming information, patient configuration of the programming (e.g., switching between groups, changing amplitudes, etc.), and daily questionnaires to determine a suitable therapy for the patient.

Chronic pain experiences are complex and unique to each patient. Pain affects numerous facets of life, including psychosocial well-being, physical activity, and the capacity to work, and other approaches are unable to accurately assess all facets during a clinic visit. Digital health platforms (e.g., mobile applications associated with the digital health platforms) supported by aspects of the present disclosure provide data which may enable clinicians and patients to track patient-reported outcomes (PROs) over time, provide patients the opportunity to self-manage pain, and educate patients about treatment options and surgical recovery, all without visiting a medical clinic. In some aspects, the systems and techniques described herein support the monitoring of real-time pain data and providing of feedback during a SCSeval period, allowing care teams to adjust therapies more efficiently as needed. Accordingly, for example, the monitoring of real-time pain data and providing of feedback during a SCSeval period may support enhancing and optimizing the SCS experience and patient-centered neuromodulation.

Non-limiting examples of real-world data from a large cohort of patients who underwent SCSeval procedures using a digital health platform supported by the present disclosure for patient education, feedback, and PROs collection throughout the procedural journey are provided at the Exhibits provided with the present disclosure and the tables included herein. The real-world data was obtained based on an observational study conducted in which patient demographics, baseline pain characteristics, SCSeval success rate, permanent implant rate, and functional improvement following temporary SCS evaluation were analyzed. The real-world data was acquired based on performing a retrospective cohort analysis of patients who underwent Spinal Cord Stimulation procedures using a mobile digital health platform supported by the present disclosure.

Examples of the digital health platform supportive of the systems and techniques of the present disclosure are later described herein. The digital health platform may provide educational resources, timely notifications, and reminders to patients throughout temporary evaluation and permanent procedures of receiving SCS therapy. In an example, a care provider invites patients to download a mobile application at a device (e.g., a smart device, a computing device, etc.) of the patient before their SCSeval (later described with reference to FIG. 1C). The mobile application may be referred to herein as a digital health platform application, a mobile app, an app, or a CGP app.

The mobile application may provide patients access to educational resources, such as Frequently Asked Questions (FAQs) and videos. The mobile application may include an integrated messaging function supportive of communications between a patient and the patient's clinical team (e.g., therapy device team). The mobile application may provide an interface via which patients may complete standard and individualized PRO surveys. In addition, the digital health platform provides secure/encrypted sharing of the PRO data (associated with the PRO surveys) with a patient's physician and care team to keep them informed of the patient's status.

Example aspects of the mobile application and the digital health platform are later described with reference to an example timeline 103 illustrated at FIG. 1C.

In some embodiments, the PROMIS-29 profile measure assesses seven domains (pain interference, ability to participate in social roles and activities, sleep disturbance, fatigue, depression, anxiety and physical function) and pain intensity. In some aspects, higher PROMIS symptom scores reflect worse symptom burden, and higher PROMIS function scores reflect better functioning. The PROMIS domain scales are scored on a T-score metric with a mean of 50 to represent the average in the US general population and a standard deviation of 10. The exception is sleep disturbance, with a score of 50 representing the average in a mix of individuals from the US general population and clinical sample experiencing sleep problems.

Statistical Analysis

The analyses described herein may be performed using R version 4.2.1, (R Foundation for Statistical Computing, Vienna, Austria) and Python 3.7 programming language (Python Software Foundation. Python Language Reference, version 3.7). In an example, alpha is set at 0.05 with adjustments for multiple comparisons.

Chronic Pain Classification

To quantify chronic pain, the systems and techniques described herein may utilize a tabulation of patient characteristics at baseline (prior to SCS therapy). The pain history questionnaire facilitates this categorization by detailing the pain's location, description, duration, treatments attempted, impact on daily life, and opioid use. The systems and techniques described herein may include compiling summary statistics for patient characteristics (age, gender), SCSeval indication, SCSeval type attempted, and location of service, but are not limited thereto.

The systems and techniques described herein support revealing sets of pain characteristics that are more likely to co-express aiming to trace predominant causes of chronic pain and how it evolves in time. The systems and techniques described herein include applying hierarchical clustering to the pain characteristics, where each characteristic may be represented by the set of patients reported on it. The distance between two characteristics may be defined as Jaccard dissimilarity score between those sets. Intuitively, aspects of the present disclosure may include considering two characteristics as being close if the characteristics appear together more frequently in the same survey than they do individually.

In some aspects, the distance between two clusters is defined as the maximum distance between all pairs of characteristics, such that each characteristic belongs to a distinct cluster. The systems and techniques described herein may include identifying clusters by pruning the resulted hierarchical tree using threshold of, for example, 0.5. In an example, using a threshold of 0.5 guarantees that any two characteristics within a cluster intersect in at least fifty percent of patients. Separate clusters of pain characteristics were calculated for patients who reported experiencing pain for 6-12 months, 1-3 years, and over 3 years, examples of which are later described herein and in the Exhibits provided with the present disclosure.

SCSeval Success Rate

At the conclusion of each SCSeval, the systems and techniques described herein may include providing data analytics based on which a care provider may determine whether the SCSeval was successful or unsuccessful. In some aspects, the data analytics may include pain metrics (e.g., pain reduction, etc.) and observed changes in the patient.

Implant Rate

The systems and techniques described herein may support monitoring the rate of permanent SCS implant after a successful SCSeval over a defined time period (e.g., over an 8-month time period with a minimum 2-month follow-up period after SCSeval). In some aspects, over the course of the defined time period (e.g., 8-month follow-up), the systems and techniques described herein may include determining cumulative implants as the proportion of patients implanted over time. In some examples, the rate may be derived at 3 and 6 months after the trial period. In some aspects, the systems and techniques described herein may include calculating the hazard rate (p/day) using a bin length of 7 days to evaluate the change in the probability of receiving a permanent SCS implant based on the absence of an implant up until that date. The systems and techniques described herein may support stratifying the analysis by service location (e.g., ambulatory service center (ASC), in-hospital, and office).

Functional Improvement

Using a standardized measure (e.g., the PROMIS-29 instrument), the systems and techniques described herein may support measuring the functional improvement at the conclusion of the SCSeval relative to the pre-trial baseline. For example, PROMIS-29 has been validated for measuring chronic pain in the surgical and back pain populations. In some aspects, the systems and techniques described herein may support utilizing a data collection tool (e.g., an online data collection tool, for example, Assessment Center) capable of using a T-score metric to score PROMIS-29 scales. Each domain's PROMIS T-Score is a standard score with a mean of 50 and a standard deviation of 10.

The systems and techniques described herein may support comparing each domain's T-score metrics between time points using a paired sample t-test. The systems and techniques described herein may include categorizing the T-scores for each domain as normal, mild, moderate, or severe according to predefined ranges. The systems and techniques described herein may include evaluating, at pre-trial baseline and trial conclusion, the proportion of patients in each category for each domain.

Quantifying the Utility of the Digital Health Platform

At the conclusion of the SCSeval, the systems and techniques described herein may include administering a feedback survey to quantify the utility of the digital health platform in preparation for the procedure, recovery, and app usability. We also assessed descriptive statistics for the time required to complete the baseline pain questionnaire and the PROMIS-29 instrument.

Patient Population and SCSeval Details

Various examples of sample patient population details (e.g., patient results, patient demographics, etc.) supportive of aspects of the present disclosure are described in the Exhibits provided with the present disclosure.

Pain History

Prior to undergoing the SCSeval procedure, the systems and techniques described herein may include prompting a patient to completing a Baseline Pain History survey, which may characterize pain location, description, duration, prior treatments attempted, impact on life, and opioid use. Various examples of the Baseline Pain History survey supportive of aspects of the present disclosure are described in the Exhibits provided with the present disclosure.

The systems and techniques described herein may support the hierarchical clustering of pain characteristics, examples of which are later described with reference to FIG. 3.

SCSeval Success

The systems and techniques described herein may support increased success rate. For example, the systems and techniques described herein may support determining whether adequate pain control has been achieved/whether a patient is eligible for permanent implant. Various examples of SCSeval Success data supportive of aspects of the present disclosure are described in the Exhibits provided with the present disclosure.

PROMIS-29 Profile Survey Results

The systems and techniques described herein may support providing data analytics based on PROMIS-29 surveys completed by patients at the beginning and conclusion of SCSeval.

In some aspects, the systems and techniques described herein may include determining whether, at baseline, the T-score of a patient (or mean T-score of a set of patients) is within a target range (e.g., normal range) for the domain of depression, within a target range (e.g., mild severity range) for the domains of sleep disturbance, fatigue, and anxiety, and within a target range (e.g., moderate range) for the domains of pain interference, ability to participate in social roles & activities, and physical function. In some cases, the systems and techniques described herein may support identifying trends associated with a patient (or set of patients). In an example implementation.

Figure 5:
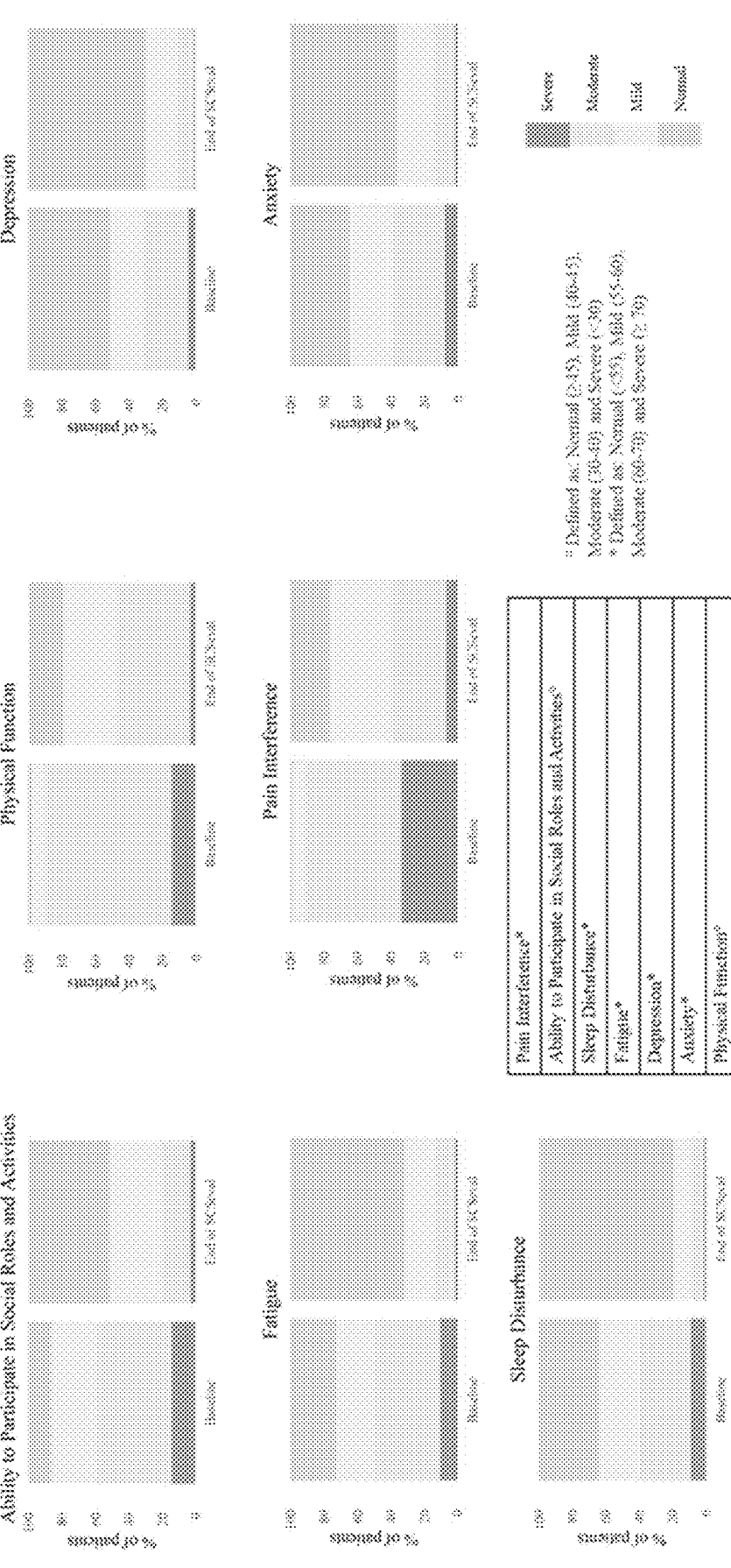
FIG. 5 illustrates examples of longitudinal changes in PROMIS-29 severity in accordance with aspects of the present disclosure.

Various examples of the data analytics and trend monitoring supported by aspects of the present disclosure are described in the Exhibits provided with the present disclosure and at FIG. 5.

App Response Survey

The surveys described herein may be implemented with survey responses that are not time-consuming or burdensome. Examples aspects of the surveys and the questions included the surveys are described in the Exhibits provided with the present disclosure.

According to example aspects of the present disclosure, the systems and techniques described herein support a digital health platform as a tool for outcome collection during the SCSeval period. In addition, the systems and techniques described herein support providing analyses for monitoring the chronic pain profiles of SCS recipients and the transition from SCSeval to permanent implant.

The digital health tools incorporated herein may remotely capture patient data and provide patients with instructions and education outside of the traditional clinic setting. Examples described herein include the utilizing of the digital health platforms in combination with data analysis techniques for clinical decision support and patient self-management of conditions (in association with increasing patient engagement and awareness).

The systems and techniques described herein include utilizing digital health tools via which patients may rapidly complete in-depth surveys. In some aspects, via the digital health tools, the systems and techniques described herein may provide pain assessments outside of the clinic, while also allowing providers to view analysis data during a SCS evaluation and evaluate the efficacy of a therapy device providing the SCS.

Evaluation of Chronic Pain before & After SCS

This digital-health platform's data as supported by the present disclosure may enable a precise quantification of chronic pain profiles, highlighting the multidimensional and pervasive nature of pain. The analytics provided by the techniques described herein may support earlier intervention with a treatment plan (e.g., SCS), which may prevent patients from developing additional conditions (e.g., opioid use disorders, mood disturbances, etc.) resulting from an untreated condition. Example results associated with evaluated durations of pain (3-12 months, 1-3 years, and 2+ years) are described in the Exhibits provided with the present disclosure. Embodiments of the present disclosure may also facilitate the development of plan modifications, which may be patient-specific or genericized for more than one patient.

In some aspects, when comparing baseline and post-SCSeval data for the population, PROMIS-29 survey results may reveal improvements (or declines) in one or more measured domains. Using the survey, the systems and techniques described herein may capture the patient experience, and the survey may function as a mechanism for care providers to receive feedback. In lieu of relying on single-item pain measures, standard surveys (e.g., PROMIS-29) utilized herein give providers a quantitative method for determining if a patient has improved significantly during the trial period.

According to example aspects of the present disclosure, the systems and techniques may support quantifying the effects of SCS with respect to a target medical condition (e.g., mental state, physical state, etc.) and other aspects and the life of the patient. For example, SCS affects multiple aspects of personal and social functioning, and the systems and techniques described herein support the use of multi-domain patient reported outcome surveys to examine the full impact of SCS on a patient's life. For example, the systems and techniques described herein support the monitoring of longitudinal standard survey results (e.g., longitudinal PROMIS-29 survey results) over follow-up periods of an appropriate length (e.g., longer periods) following permanent SCS implantation.

Permanent Implant Rate

In some aspects, the data analytics and recommendations provided by the systems and techniques described herein may support an increased conversion rate (e.g., about 72.4%) from temporary SCS/SCSeval to a permanent implant compared to the nationwide rate (64%), among other advantages.

Examples of test results related to the conversion rate are described in the Exhibits provided with the present disclosure.

Patient Perspectives on Digital Health

Example aspects of the digital health platform described herein may provide a user-friendly experience and useful patient guidance associated with the SCSeval procedure's preparation and recovery. In the example context of neuromodulation, digital health tools implemented with the digital health platform described herein can provide the ability to effectively engage patients in their therapy journey and enable providers to evaluate the effectiveness of treatment based on patient-reported outcomes.

Additional and/or Alternative Example Implementations

The data analytics described herein associated with determining objective measures of chronic pain and providing recommendations for chronic pain management may be implemented using any appropriate data (e.g., device data, survey responses, etc.) described herein. It is to be understood that the data analytics may be implementing using data additional and/or alternative to the data described herein. For example, the data analytics may further be based on sociodemographic characteristics (e.g., according to race, ethnicity, socioeconomic status, etc.) and electronic medical record data (e.g., dosages, types of medications patients used, etc.). Various example aspects of the additional and/or alternative data are described in the Exhibits provided with the present application.

The systems and techniques described herein may support providing personalized reminders for survey and task completion, presenting survey results back to patients, and allowing for direct contact with providers through a digital health platform application described herein for increasing patient engagement.

Other example implementations supported by aspects of the present disclosure include quantifying the impact of permanent SCS based on analyzing longitudinal data from patients' post-implant SCS PROMIS-29 surveys. For example, other example implementations may support distinguishing the patient experience and pain characteristics of SCS indications (e.g., failed back surgery syndrome, chronic regional pain syndrome, and painful diabetic neuropathy).

According to example aspects of the present disclosure, the digital health platform described herein may support patient use of digital health technology as part of the SCS journey to enhance the patient experience and allow for the robust collection of patient-reported outcomes. The systems and techniques described herein support characterizing the pain profiles of patients undergoing SCSeval and examining the trial-to-permanent conversion rates. The systems and techniques described herein provide a digital health platform (and digital health platform application) which may enable clinicians and representatives to track and quantify (e.g., with increased accuracy and insight) changes in chronic pain, thereby providing more insight into the decision to permanently implant SCS.

The systems and techniques described herein support the characterization of multiple health-related quality of life domains affected by pain, as well as improvement in all domains among SCSeval-treated patients, based on data acquired using a standardized measure (e.g., PROMIS-29). Accordingly, for example, utilizing the digital health platform and aspects thereof in a SCS evaluations as described herein may enhance patient experiences and data collection during the process of undergoing an SCSeval and deciding to proceed with a permanent implant.

Other example implementations supported by aspects of the present disclosure include characterizing the long-term pain outcomes of patients with permanent SCS implants and determining how pain etiology influences postoperative outcomes, based on data acquired using a standardized measure (e.g., PROMIS-29). For example, based on the characterizations, the systems and techniques described herein may provide clinicians with an increased understanding of best practices and enable the creation of therapy options tailored to the etiology of pain and specific pain subtypes.

Various example aspects supported by the present disclosure are described herein with reference to the following Figures. Other example aspects of the Figures are described in the Exhibits provided with the present application.

Figure 1A:
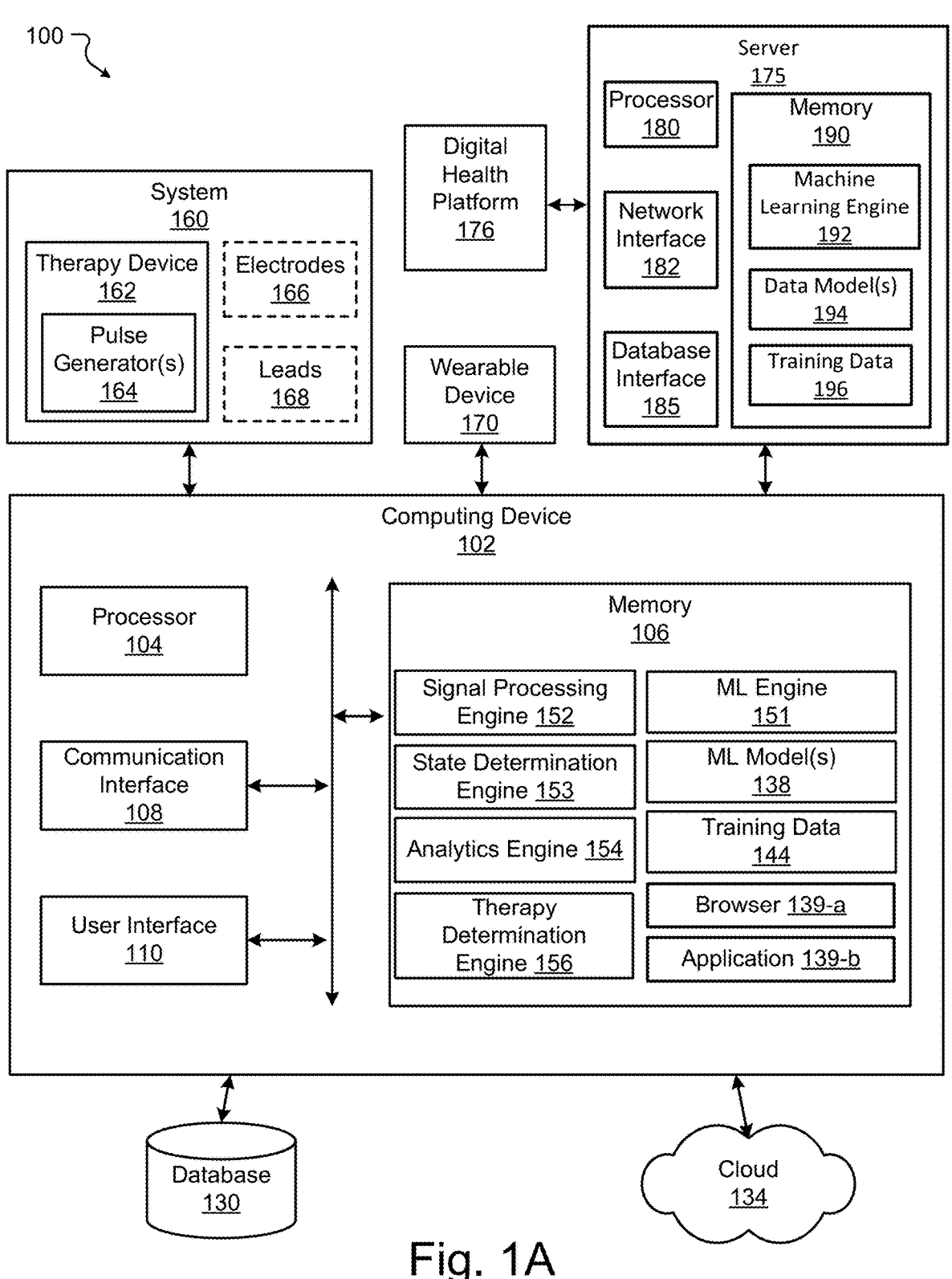
FIG. 1A illustrates an example of a system that supports aspects of the present disclosure.

FIG. 1A illustrates an example of a system 100 that supports aspects of the present disclosure.

The system 100 includes a computing device 102, a database 130, a cloud network 134 (or other network), a system 160, and/or a wearable device 170. Systems according to other implementations of the present disclosure may include more or fewer components than the system 100. For example, the system 100 may omit and/or include additional instances of one or more components of the computing device 102, the database 130, and/or the cloud network 134. In an example, the system 100 may omit any instance of the computing device 102, the database 130, and/or the cloud network 134. The system 100 may support the implementation of one or more other aspects of one or more of the methods disclosed herein.

The computing device 102 includes a processor 104, a memory 106, a communication interface 108, and a user interface 110. Computing devices according to other implementations of the present disclosure may include more or fewer components than the computing device 102. The computing device 102 may be, for example, a control device including electronic circuitry associated with providing control signals to a therapy device 162 of the system 160.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the database 130, the cloud network 134 (or other network), the system 160, and/or the wearable device 170.

The processor 104 (or multiple processors 104) may provide instructions to the therapy device 162, the leads 168, the electrodes 166, or other components of the system 100 not explicitly shown or described herein for applying a neuromodulation therapy, stimulation, performing measurements (e.g., biometric measurements, cardiac metrics, ECAPs, etc.), and analyzing the same, as described herein. In some examples, the one or more processors 104 may be part of the therapy device 162 or part of a control unit for the system 100 (e.g., where the control unit is in communication with the therapy device 162 and/or other components of the system 100).

The therapy device 162 and/or wearable device 170 may be programmed to measure and record movements of a patient (e.g., for the purpose of life, sleep, and activity tracking). For example, the therapy device 162 and/or wearable device 170 may comprise an accelerometer and/or other components that are designed to track and record movements of the patient (e.g., whether the patient is moving, not moving, laying down, standing up, running, walking, etc.).

Additionally, the leads 168 and/or electrodes 166 disposed at the distal end of the leads 168 may be programmed to measure a physiological response of the patient 148.

In some examples, the physiological response may comprise an evoked response (e.g., ECAP measurement) based on applying therapy (e.g., a therapeutic electrical signal, for example, a stimulation signal) generated by the therapy device 162 to the spinal cord (e.g., and/or to nearby nerves). In another example, the physiological response may include spontaneous activity (e.g., spontaneous physiological responses) by the patient. Additionally or alternatively, as described herein, the physiological response may comprise biometric data, for example, cardiac signals (e.g., HR, HRV, respiration, other cardiac electrogram-related measurements, etc.) of the patient, before, during, and after the therapeutic electrical signal is applied. In some examples, the therapy device 162 may be programmed to measure and record the biometric data via an electrode vector and/or electrodes 166 placed on an outer surface of the therapy device 162 and/or within the therapy device 162, in addition or alternative to the leads 168 and/or electrodes 166.

The memory 106 may be or include RAM, DRAM, SDRAM, other solid-state memory, any memory described herein, or any other tangible, non-transitory memory for storing computer-readable data and/or instructions. The memory 106 may store information or data associated with completing, for example, any step of the methods described herein, or of any other methods. The memory 106 may store, for example, instructions and/or machine learning models that support one or more functions of the computing device 102, the system 160, and/or the wearable device 170. For instance, the memory 106 may store content (e.g., instructions and/or machine learning models) that, when executed by the processor 104, enable features and/or engines (e.g., machine learning engine 151, signal processing engine 152, state determination engine 153, analytics engine 154, therapy determination engine 156, etc.) described herein. Such content, if provided as in instruction, may, in some implementations, be organized into one or more applications, modules, packages, layers, or engines.

Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the computing device 102, the database 130, the cloud network 134, the system 160, and/or the wearable device 170.

The computing device 102 may also include a communication interface 108. The communication interface 108 may be used for receiving data or other information from an external source (e.g., the database 130, the cloud network 134, the system 160, the wearable device 170, and/or any other system or component separate from the system 100), and/or for transmitting instructions, data (e.g., control signals, data signals, waveforms, etc.), or other information to an external system or device (e.g., another computing device 102, the database 130, the cloud network 134, the system 160, the wearable device 170, and/or any other system or component not part of the system 100).

The communication interface 108 may include one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some implementations, the communication interface 108 may support communication between the device 102 and one or more other processors 104 or computing devices 102, whether to reduce the time needed to accomplish a computing-intensive task or for any other reason.

The computing device 102 may also include one or more user interfaces 110. The user interface 110 may be or include a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some implementations, the user interface 110 may support user modification (e.g., by a surgeon, medical personnel, a patient, etc.) of instructions to be executed by the processor 104 according to one or more implementations of the present disclosure, and/or to user modification or adjustment of a setting of other information displayed on the user interface 110 or corresponding thereto.

In some implementations, the computing device 102 may utilize a user interface 110 that is housed separately from one or more remaining components of the computing device 102. In some implementations, the user interface 110 may be located proximate one or more other components of the computing device 102, while in other implementations, the user interface 110 may be located remotely from one or more other components of the computer device 102.

The system 160 may include a therapy device 162, electrodes 166, and leads 167. The therapy device 162 may include an implantable pulse generator (e.g., pulse generator 164). The therapy device 162 may be configured to generate a current (e.g., therapeutic electrical signal, stimulation signal, electrical stimulation signal, etc.) associated with delivering therapy (e.g., neuromodulation therapy, SCS, peripheral nerve stimulation, etc.), and the leads 167 and the electrodes 166 may comprise a plurality of electrodes configured to carry the current from the therapy device 162 and apply the current to an anatomical element based on the electrodes being implanted on or near the anatomical element (e.g., stimulation target, for example, the spinal cord of the patient and/or nearby nerves to the spinal cord). In some examples, the therapy device 162, leads 167, and electrodes 166 may be configured to measure a physiological response of the patient 148 (e.g., prior to applying the current to the anatomical element, during application of the current, after the current is applied, etc.). In some example implementations, the therapy device 162 may be implemented as a leadless stimulation device.

The system 160 may communicate with the computing device 102 to receive instructions for applying a current to the anatomical element and/or delivering therapy (e.g., electrical stimulation, pharmacological agent, etc.) to the anatomical element. The system 160 may also provide data (such as data received from an electrodes 166 capable of recording data), which may be used to optimize the electrodes 166 (e.g., optimize electrode placement) and/or to optimize parameters of the current generated by the therapy device 162.

Signal processing engine 152 enables the processor 104 to implement features associated with processing of data or data signals (e.g., from a therapy device 162, wearable device 170, other appropriate device supported by the system 100, etc.) described herein.

State determination engine 153 enables the processor 104 to implement features associated with determining one or more states of a patient in association with at least one health domain as described herein.

Analytics engine 154 enables the processor 104 to implement features associated with providing data analytics as described herein.

Therapy determination engine 156 enables the processor 104 to implement features associated with determining parameters (e.g., stimulation parameters associated with delivering therapy) and recommendations as described herein.

The therapy determination engine 156 enables the processor 104 to determine one or more parameters for applying the neuromodulation therapy to the anatomical element based at least in part on one or more outputs by the machine learning models 138. In an example, the therapy determination engine 156 may determine parameters or instructions that cause the therapy device 162 to employ the pulse generator 164 to generate a stimulus or that cause the therapy device 162 to deliver other therapy (e.g., a pharmacological agent, etc.). In some aspects, the therapy determination engine 156 may be referred to as a clinician programmer application.

The computing device 102 may render a presentation (e.g., visually, audibly, using haptic feedback, etc.) of an application 139 (e.g., a browser application 139-a, an application 139-b). The application 139-b may be an application associated with implementing one or more features described herein in accordance with aspects of the present disclosure.

The computing device 102 may render a presentation (e.g., visually, audibly, using haptic feedback, etc.) of an application 139 (e.g., a browser application 139-a, an application 139-b). The application 139-b may be an application associated with executing, controlling, and/or monitoring performance of a generator 105 as described herein. For example, the application 139-b may enable control of the computing device 102 and/or a generator 105 described herein.

In an example, the computing device 102 may render the presentation via the user interface 110. The user interface 110 may include, for example, a display (e.g., a touchscreen display), an audio output device (e.g., a speaker, a headphone connector), or any combination thereof. In some aspects, the applications 139 may be stored on the memory 106. In some cases, the applications 139 may include cloud-based applications or server-based applications (e.g., supported and/or hosted by the database 130 or the server 175). Settings of the user interface 110 may be partially or entirely customizable and may be managed by one or more users, by automatic processing, and/or by artificial intelligence.

In an example, any of the applications 139 (e.g., browser application 139-a, application 139-b) may be configured to receive data in an electronic format and present content of data via the user interface 110. For example, the applications 139 may receive data from a generator 105, another computing device 102, the server 175, and/or the database 130 via the cloud network 134, and the computing device 102 may display the content via the user interface 110.

The processor 104 may utilize data stored in memory 106 as a neural network. The neural network may include a machine learning architecture. In some aspects, the neural network may be or include one or more classifiers. In some other aspects, the neural network may be or include any machine learning network such as, for example, a deep learning network, a convolutional neural network, a reconstructive neural network, a generative adversarial neural network, or any other neural network capable of accomplishing functions of the computing device 102 described herein. Some elements stored in memory 106 may be described as or referred to as instructions or instruction sets, and some functions of the computing device 102 may be implemented using machine learning techniques. The neural network may be referred to as a machine learning engine 151.

The neural network architecture may support various inputs supportive of implementing aspects of the present disclosure. For example, the neural network architecture may support generating outputs based on model inputs including, but not limited to, device data (e.g., provided by wearable device 170, provided by therapy device 162), survey data, and the like described herein.

The neural network architecture may include various appropriate model types supportive of implementing aspects of the present disclosure. For example, the neural network architecture may include statistical machine learning models (e.g., linear regression, logistic regression, decision trees, random forest, Naïve bayes, ensemble methods, support vector machines, k-nearest neighbor, etc.). In some examples, the neural network architecture may include deep learning models (e.g., convolutional neural network, recurrent neural network, deep reinforcement network, deep belief network, transformer network, etc.). In some examples, the machine learning model(s) 138 may include vector machines (SVMs), convolutional neural network (CNN) models, or other machine learning models appropriate with implementing aspects of the present disclosure as described herein.

The neural network architecture may support unsupervised machine learning algorithms (e.g., principal component analysis (PCA) algorithms), semi-supervised machine learning algorithms, and supervised machine learning algorithms. The neural network architecture may support locked execution modes and continuous learning execution modes. The neural network architecture may support providing outputs including content, classifications, predictions, recommendations, and decisions.

The processor 104 may support machine learning model(s) 138 which may be trained and/or updated based on data (e.g., training data 146) provided or accessed by any of the computing device 102, the database 130, the cloud network 134, the system 160, and/or the wearable device 170. The machine learning model(s) 138 may be built and updated by the computing device 102 based on the training data 146 (also referred to herein as training data and feedback).

For example, the machine learning model(s) 138 may be trained with one or more training sets included in the training data 146. In some aspects, the training data 146 may include multiple training sets. In an example, the training data 146 may include aspects of the data (e.g., device data, device utilization data, device metrics, objective measures of a chronic condition, survey data, etc.) and states described herein.

In some examples, based on the data, the neural network may generate one or more algorithms (e.g., processing algorithms 142) supportive of the features described herein.

The server 175 may include a processor 180, a network interface 181, database interface instructions 185, and a memory 190. In some examples, components of the server 175 (e.g., processor 180, network interface 181, database interface 185, memory 190) may communicate over a system bus (e.g., control busses, address busses, data busses) included in the server 175. The processor 180, network interface 181, and memory 190 of the server 175 may include examples of aspects of the processor 104, communication interface 108, and memory 106 of the computing device 102 described herein.

For example, the processor 180 may be configured to execute instruction sets stored in memory 190, upon which the processor 180 may enable or perform one or more functions of the server 175. In some examples, the server 175 may transmit or receive packets to one or more other devices (e.g., a computing device 102, the database 130, another server 175) via the cloud network 134, using the network interface 181. Communications between components (e.g., processor 180, memory 190) of the server 175 and one or more other devices (e.g., a computing device 102, the database 130, etc.) connected to the cloud network 134 may, for example, flow through the network interface 181.

In some examples, the database interface instructions 185 (also referred to herein as database interface 185), when executed by the processor 180, may enable the server 175 to send data to and receive data from the database 130. For example, the database interface instructions 185, when executed by the processor 180, may enable the server 175 to generate database queries, provide one or more interfaces for system administrators to define database queries, transmit database queries to one or more databases (e.g., database 130), receive responses to database queries, access data associated with the database queries, and format responses received from the databases for processing by other components of the server 175.

The memory 190 may be configured to store instruction sets, neural networks, and other data structures (e.g., depicted herein) in addition to temporarily storing data for the processor 180 to execute various types of routines or functions. For example, the memory 190 may be configured to store program instructions (instruction sets) that are executable by the processor 180 and provide functionality of a machine learning engine 192. One example of data that may be stored in memory 190 for use by components thereof is a data model(s) 194 (e.g., any data model described herein, a neural network model, etc.) and/or training data 196.

The data model(s) 194 and the training data 196 may include examples of aspects of the data model(s) 138 and the training data 144 described with reference to the computing device 102. The machine learning engine 192 may include examples of aspects of the machine learning engine 151 described with reference to the computing device 102.

Though not shown, the system 100 may include a controller, though in some implementations the system 100 may not include the controller. The controller may be an electronic, a mechanical, or an electro-mechanical controller. The controller may comprise or may be implemented by any processor (e.g., processor 104) described herein. The controller may comprise a memory storing instructions for executing any of the functions or methods described herein as being carried out by the controller. In some implementations, the controller may be configured to simply convert signals received from the computing device 102 (e.g., via a communication interface 108) into commands for operating the system 160 (and more specifically, for actuating the therapy device 162 and the pulse generator(s) 164 thereof). In other implementations, the controller may be configured to process and/or convert signals received from the system 160 or the wearable device 170. Further, the controller may receive signals from one or more sources (e.g., system 160, wearable device 170) and may output signals to one or more sources.

The database 130 may additionally or alternatively store, for example, training data 144, classification data, and the like. The database 130 may additionally or alternatively store, for example, location or coordinates of an implantable medical device.

The database 130 may be configured to provide any such information to the computing device 102 or to any other device of the system 100 or external to the system 100, whether directly or via the cloud network 134. In some implementations, the database 130 may include treatment information (e.g., a pain management plan, a therapy plan) associated with a patient. In some implementations, the database 130 may be or include part of a hospital image storage system, such as a picture archiving and communication system (PACS), a health information system (HIS), and/or another system for collecting, storing, managing, and/or transmitting electronic medical records including image data.

In some aspects, the computing device 102 may communicate with a server(s) and/or a database (e.g., database 130) directly or indirectly over a communications network (e.g., the cloud network 134). The communications network may include any type of known communication medium or collection of communication media and may use any type of protocols to transport data between endpoints. The communications network may include wired communications technologies, wireless communications technologies, or any combination thereof.

Wired communications technologies may include, for example, Ethernet-based wired local area network (LAN) connections using physical transmission mediums (e.g., coaxial cable, copper cable/wire, fiber-optic cable, etc.). Wireless communications technologies may include, for example, cellular or cellular data connections and protocols (e.g., digital cellular, personal communications service (PCS), cellular digital packet data (CDPD), general packet radio service (GPRS), enhanced data rates for global system for mobile communications (GSM) evolution (EDGE), code division multiple access (CDMA), single-carrier radio transmission technology (1×RTT), evolution-data optimized (EVDO), high speed packet access (HSPA), universal mobile telecommunications service (UMTS), 3G, long term evolution (LTE), 4G, and/or 5G, etc.), Bluetooth®, Bluetooth® low energy, Wi-Fi, radio, satellite, infrared connections, and/or ZigBee® communication protocols.

The Internet is an example of the communications network that constitutes an Internet Protocol (IP) network consisting of multiple computers, computing networks, and other communication devices located in multiple locations, and components in the communications network (e.g., computers, computing networks, communication devices) may be connected through one or more telephone systems and other means. Other examples of the communications network may include, without limitation, a standard Plain Old Telephone System (POTS), an Integrated Services Digital Network (ISDN), the Public Switched Telephone Network (PSTN), a Local Area Network (LAN), a Wide Area Network (WAN), a wireless LAN (WLAN), a Session Initiation Protocol (SIP) network, a Voice over Internet Protocol (VOIP) network, a cellular network, and any other type of packet-switched or circuit-switched network known in the art. In some cases, the communications network may include of any combination of networks or network types. In some aspects, the communications network may include any combination of communication mediums such as coaxial cable, copper cable/wire, fiber-optic cable, or antennas for communicating data (e.g., transmitting/receiving data).

The computing device 102 may be connected to the cloud network 134 via the communication interface 108, using a wired connection, a wireless connection, or both. In some implementations, the computing device 102 may communicate with the database 130 and/or an external device (e.g., a computing device) via the cloud network 134.

The system 100 or similar systems may be used, for example, to carry out one or more aspects of any of the techniques and process flows described herein. The system 100 or similar systems may also be used for other purposes.

Figure 1B:
FIG. 1B illustrates an example framework in accordance with aspects of the present disclosure.

FIG. 1B illustrates an example framework 101 supported by the system 100 and techniques described herein. Example components included in the framework 101 may be implemented by aspects of the system 100. The example components include, but are not limited to, digital health platform 176, a survey 177, data science analytics 171, insights 172, chronic pain states 174, Decision data 178, and state trends and therapy data 179.

Digital health platform 176 may be implemented by aspects of the system 100 described herein. For example, the digital health platform 176 may be supported or implemented by one or more servers 175.

The survey 177 may be a standardized questionnaire (e.g., a PROMIS-29 questionnaire) including a set of questions associated with multiple health domains. For example, the survey 177 may be a PROMIS-29 questionnaire for assessing seven domains (pain interference, ability to participate in social roles and activities, sleep disturbance, fatigue, depression, anxiety and physical function) and pain intensity. Example aspects of the survey 177 are described in the Exhibits provided with the present disclosure.

Data science analytics 171 includes aspects of data analytics (e.g., patient analytics, cohort analysis, statistical analysis, etc.) described herein. Data science analytics 171 may include analytics of real-world data of patients (e.g., obtained from survey 177).

Insights 172 may include data generated and provided by the system 100. The system 100 may provide insights 172 on real-world data associated with a patient and long-term treatment outcomes. For example, the system 100 may provide insights 172 to a clinician for determining whether to a patient is a candidate for a permanent SCS implant.

In some aspects, the system 100 may provide insights 172 based on data included in the survey 177 (e.g., responses to a PROMIS-29 questionnaire), without additional data. Accordingly, for example, the system 100 may support providing insights 172 based on a relatively limited amount of information, while generating information based on which the system 100 and/or a clinician may tailor treatments for a patient. In some other example implementations, the system 100 may provide insights 172 based on data included in the survey 177 and additional data (e.g., demographics information, chronic pain history, and the like).

Insights 172 may include phenotypes of chronic pain. In some aspects, insights 172 may include data indicative of how phenotype may change for a patient in response to exposure to SCS therapy. The system 100 may generate insights 172 using cluster analysis techniques described herein. Insights 172 may be provided via one or more visualizations supported by the system 100. Non-limiting examples of the visualizations are illustrated at FIGS. 5-7, 9A, 9B, 11A, and 11B.

Chronic pain state data 174 may include data associated with five states (e.g., A, B, C, D, E) described herein that define the chronic pain state of a patient. In an example, state A through state E may indicate relatively increasing amounts of severity of chronic pain. For example, state A may indicate the least severity and state E may represent the highest severity of chronic pain.

The chronic pain state data 174 may include temporal information associated with the states (e.g., change in states over time). Example aspects of the chronic pain state data 174 are described with reference to FIGS. 5-7, 9A, 9B, 11A, and 11B and at the Exhibits provided with the present disclosure. The chronic pain state data 174 may be stored in one or more electronic data records (e.g., as one or more entries in the memory 106, the database 130, or the like).

Decision data 178 may include decisions based on temporal trends. In some aspects, Decision data 178 may include population trends and patient trends described herein.

State trends and therapy data 179 may include an integration of data associated with state trends and therapy delivery. For example, state trends and therapy data 179 may include correlational data between state trends (e.g., changes in state) and therapy delivery.

The example components enable clinical decision support in accordance with aspects of the present disclosure.

Figure 1C:
FIG. 1C illustrates an example timeline for engaging with digital health platform in accordance with aspects of the present disclosure.

FIG. 1C illustrates an example timeline 103 for engaging with digital health platform 176 in accordance with aspects of the present disclosure. In an example, for a patient being considered for SCS and having chronic pain, the timeline 103 represents an example of how the patient may engage with the digital health platform 176 via a mobile application (e.g., application 139-*b*) associated with the digital health platform 176.

Examples of the digital health platform 176 supportive of the system 100 and techniques of the present disclosure are described herein. A care provider invites patients to download a mobile application at a computing device 102 (e.g., a smart device, a computing device, etc.) of the patient before their SCSeval (at 180 of FIG. 1C). The patient may download the mobile application at 180 of the timeline 103.

The mobile application may be referred to herein as a digital health platform application, a mobile app, an app, or a CGP app. The mobile application may provide patients access to educational resources, such as Frequently Asked Questions (FAQs) and videos. The mobile application may include an integrated messaging function supportive of communications between a patient and the patient's clinical team (e.g., therapy device team). The mobile application may provide an interface via which patients may complete standard and individualized surveys (e.g., PRO surveys). In addition, the digital health platform 176 provides secure/encrypted sharing of the PRO data (associated with the PRO surveys) with a patient's physician and care team to keep them informed of the patient's status.

An example implementation is described with reference to the timeline 103. After the patient completes enrollment in the digital health platform 176 (at 180), the digital health platform 176 may provide (at 182) a baseline pain history survey and/or a PROMIS-29 survey to the patient. For example, at 182, the digital health platform 176 may provide the patient with the baseline pain history survey and/or the PROMIS-29 survey. In some aspects, the digital health platform may provide the baseline pain history survey and/or PROMIS-29 survey prior to SCS evaluations (e.g., SCSeval 8-10) implemented at 183 of the timeline 103. The digital health platform may again provide the patients the PROMIS-29 survey at the conclusion of the evaluation period (e.g., at 185 of the timeline 103). Example aspects of the baseline pain history survey, PROMIS-29 survey, and SCS evaluations are described in the Exhibits provided with the present disclosure.

In some aspects, the digital health platform 176 may prompt the patient to complete one or more additional surveys (e.g., PROMIS-29 surveys) at one or more temporal instances 188-*a* (e.g., at 4 weeks) through 188-d (e.g., at 3 months).

The PROMIS-29 profile measure assesses seven domains (pain interference, ability to participate in social roles and activities, sleep disturbance, fatigue, depression, anxiety and physical function) and pain intensity. In some aspects, higher PROMIS symptom scores reflect worse symptom burden, and higher PROMIS function scores reflect better functioning. The PROMIS domain scales are scored on a T-score metric with a mean of 50 to represent the average in the US general population and a standard deviation of 10. The exception is sleep disturbance, with a score of 50 representing the average in a mix of individuals from the US general population and clinical sample experiencing sleep problems.

In an example implementation, at the conclusion of the SCSeval period 184, the digital health platform may collect a feedback survey (at 185) to characterize the user experience and utility of the platform. Example aspects of the feedback survey are described at Exhibits provided with the present disclosure, Supplementary Material 3. The SCS eval period 184 may be any defined temporal period. In some example implementations, the SCSeval period 184 may be between 3 to 10 days. Examples of pain history survey data, PROMIS-29 survey data, and feedback survey data collected during the SCSeval period 184 are described herein and at Exhibits provided with the present disclosure.

Figure 2A:
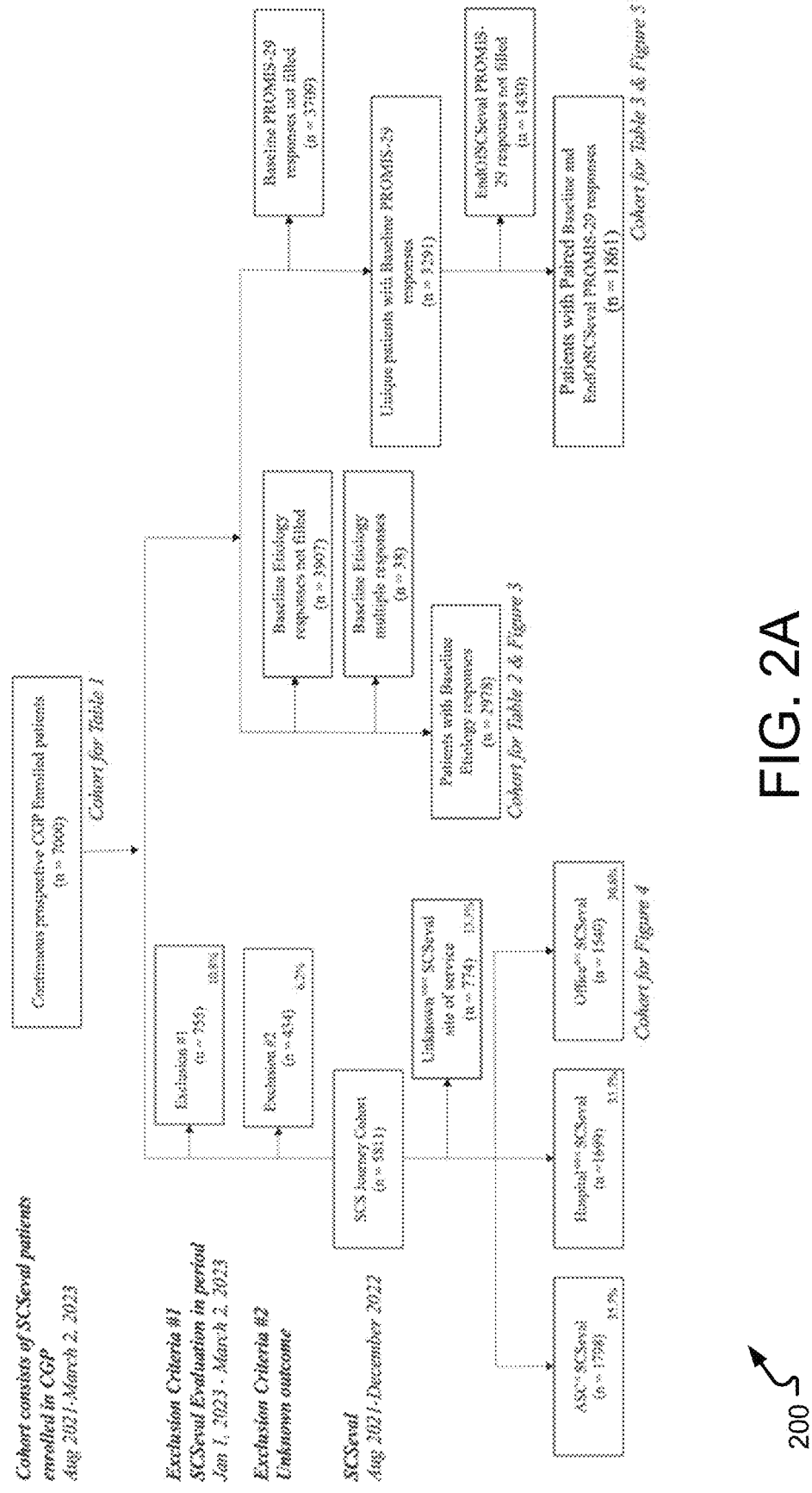
FIGS. 2A and 2B illustrate example cohort diagrams in accordance with aspects of the present disclosure.
Figure 2B:
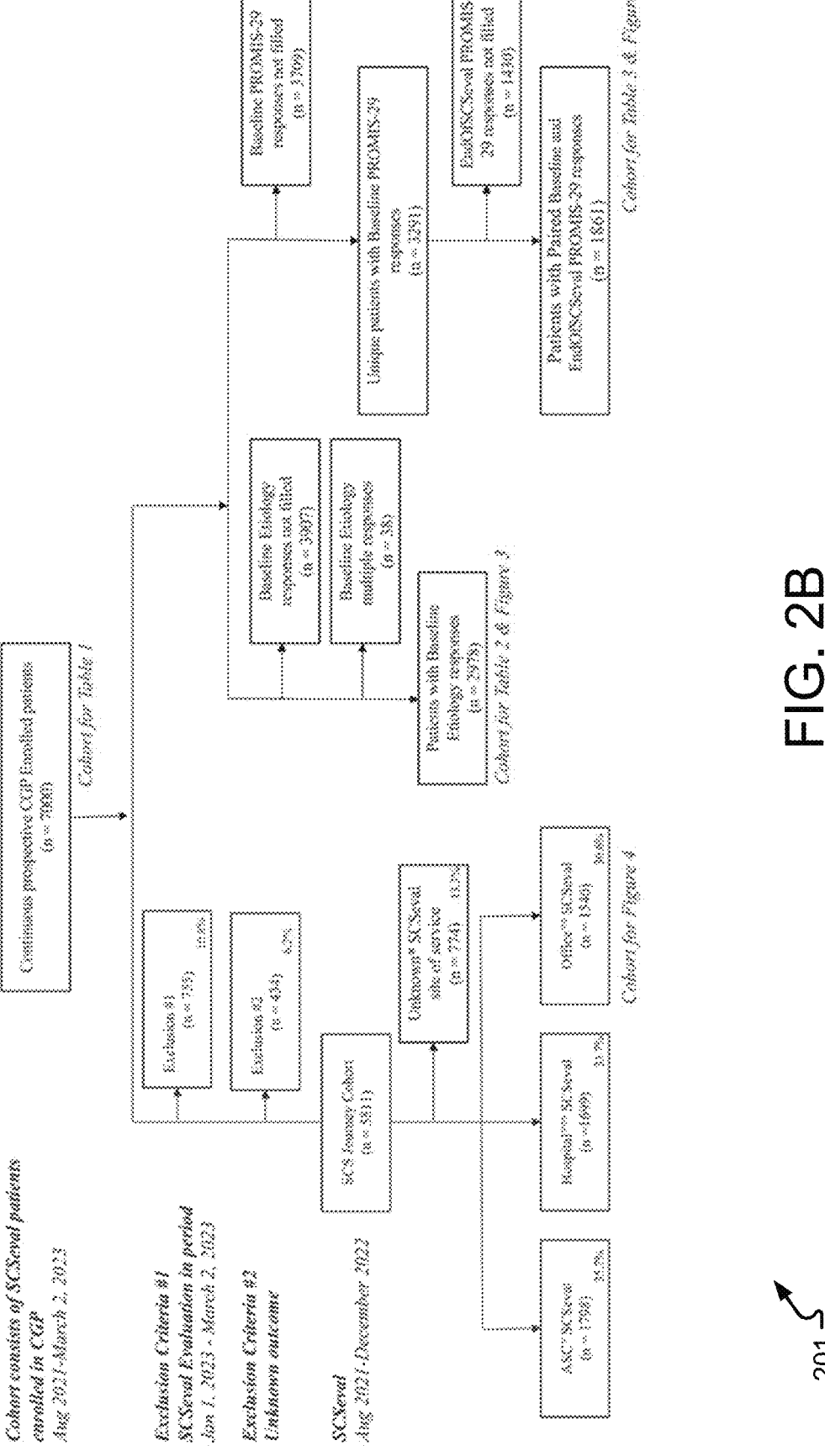

FIGS. 2A and 2B illustrate example cohort diagrams 200 and 201 of Patients who underwent SCS evaluation. The cohort diagrams 200 and 201 illustrate example inclusion and exclusion of patients, as well as patients who completed SCS evaluations and PROMIS-29 surveys.

Referring to FIGS. 2A and 2B, the term 'ASC' refers to ambulatory surgical center. Defined as a freestanding facility, other than a physician's office, where surgical and diagnostic services are provided on an ambulatory basis. The term 'Office' refers to a location, other than a hospital, skilled nursing facility (SNF), military treatment facility, community health center, state or local public health clinic, or intermediate care facility (ICF), where the health professional routinely provides health examinations, diagnosis, and treatment of illness or injury on an ambulatory basis. The term 'Hospital' refers to a facility, other than psychiatric, which primarily provides diagnostic, therapeutic (both surgical and nonsurgical), and rehabilitation services by, or under, the supervision of physicians to patients admitted for a variety of medical conditions.

Various example aspects of the data associated with the cohort diagrams 200 and 201, study cohort, data source, and data processing/variable transformation are described in the Exhibits provided with the present application.

Figure 3:
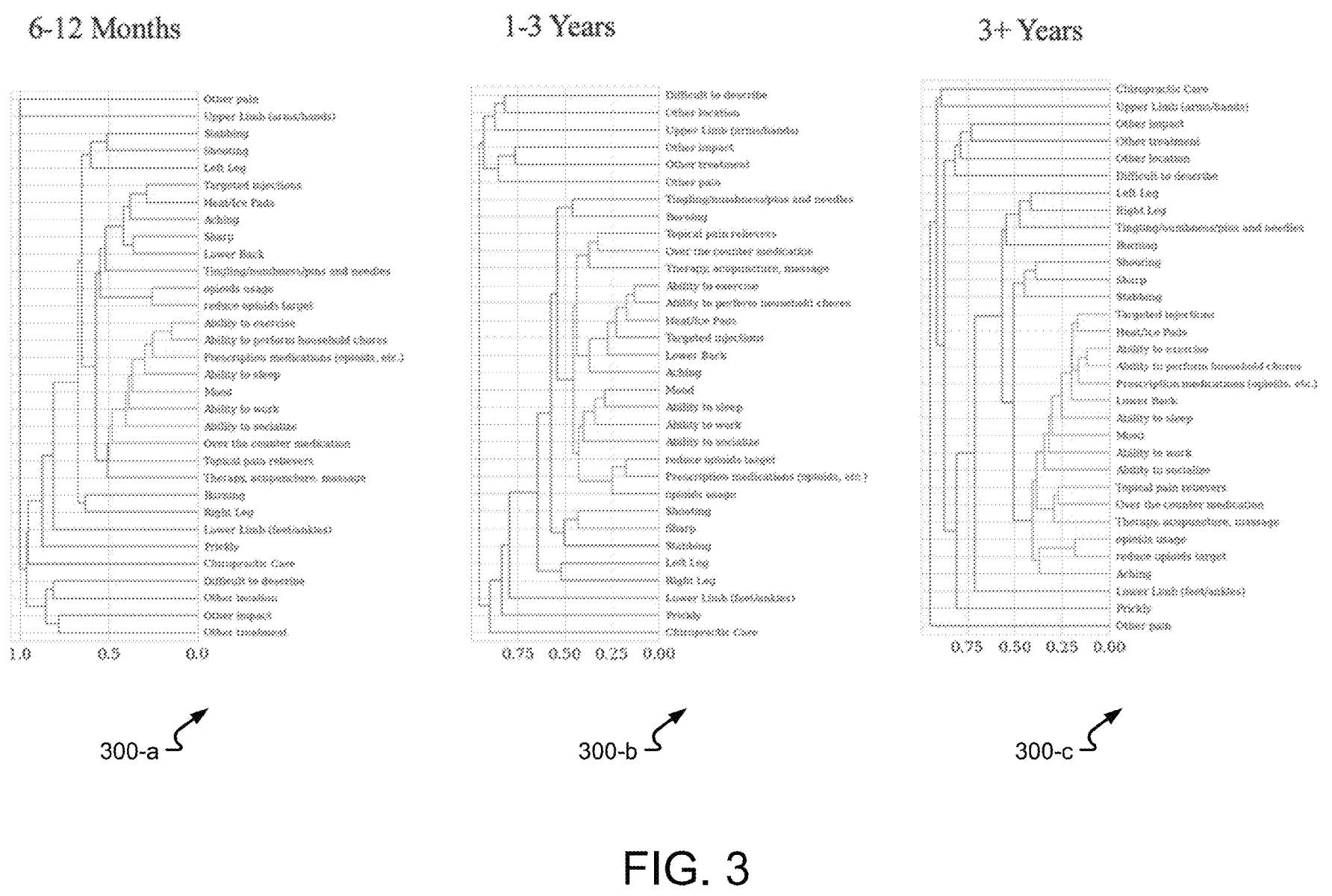

FIG. 3 illustrates example clusters 300 of chronic pain characteristics which may be determined using hierarchical clustering in accordance with aspects of the present disclosure.

Cluster 300-*a* is of pain characteristics at 6-12 months, cluster 300-*b* is of pain characteristics at 1-3 years, and cluster 300-*c* is of pain characteristics at 3+ years among patients who completed pain surveys. In accordance with aspects of the present disclosure, the plots illustrating the clusters 300 were made using Jaccard distance and a complete-link linkage method with a cutting threshold of 0.5.

In the example of FIG. 3, data from patients who reported experiencing discomfort for 6-12 months revealed three clusters: 1) Sharp pain, lower back pain, aching pain, and the use of targeted injections & heat/ice pads; 2) Ability to exercise, ability to perform chores, ability to sleep, ability to work, ability to socialize, mood, prescription medications, over the counter medications, & topical pain relievers; 3) Opioid use and a target to reduce opioid use. At 1 to 3 years of pain, two new clusters emerged: 1) tingling/numbness/pins-and-needles pain and scaring pain; 2) shooting pain and sharp pain. At 3+ years of pain, three clusters emerged, with one cluster combining most of the previous clusters and another cluster combining left and right leg pain with tingling/numbness/pins-and-needles pain.

Figure 4:
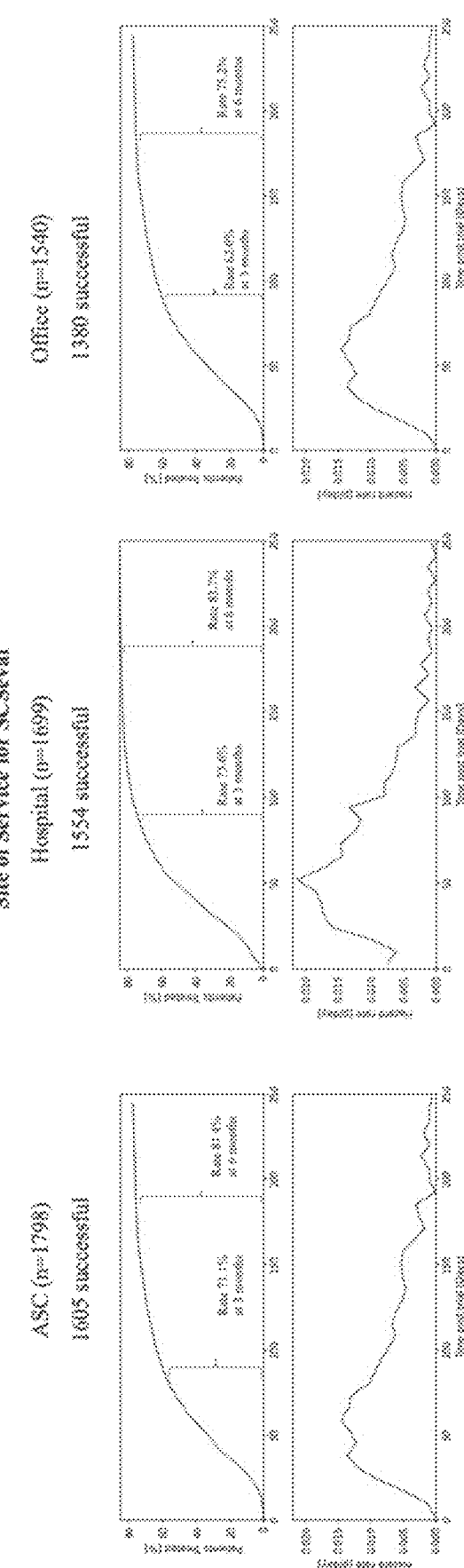
FIG. 4 illustrates example plots associated with permanent SCS implant rate in accordance with aspects of the present disclosure.

FIG. 4 illustrates example plots associated with permanent SCS implant rate in accordance with aspects of the present disclosure.

The example plots show the cumulative SCSeval conversion rate over time, as well as the hazard rate per day (p/day) after successful SCSeval procedures. The hazard rate (p/day) was derived to evaluate change in probability of receiving a permanent SCS implant conditional on absence of an implant until that date.

FIG. 5 illustrates examples of longitudinal changes in PROMIS-29 severity in accordance with aspects of the present disclosure.

Referring to FIG. 5, example stacked bar plots illustrate the percentage of patients for which severity (PROMIS-29 severity) is Severe, Moderate, Mild, and Normal at Baseline (e.g., according to a baseline pain survey described herein) and End of SCSeval (e.g., according to a PROMIS-29 survey). In the example of FIG. 5, the proportion of patients in the severe category decreased across all PROMIS domains by the end of the SCSeval period, while the proportion of patients in the normal and mild categories increased.

Figure 6A:
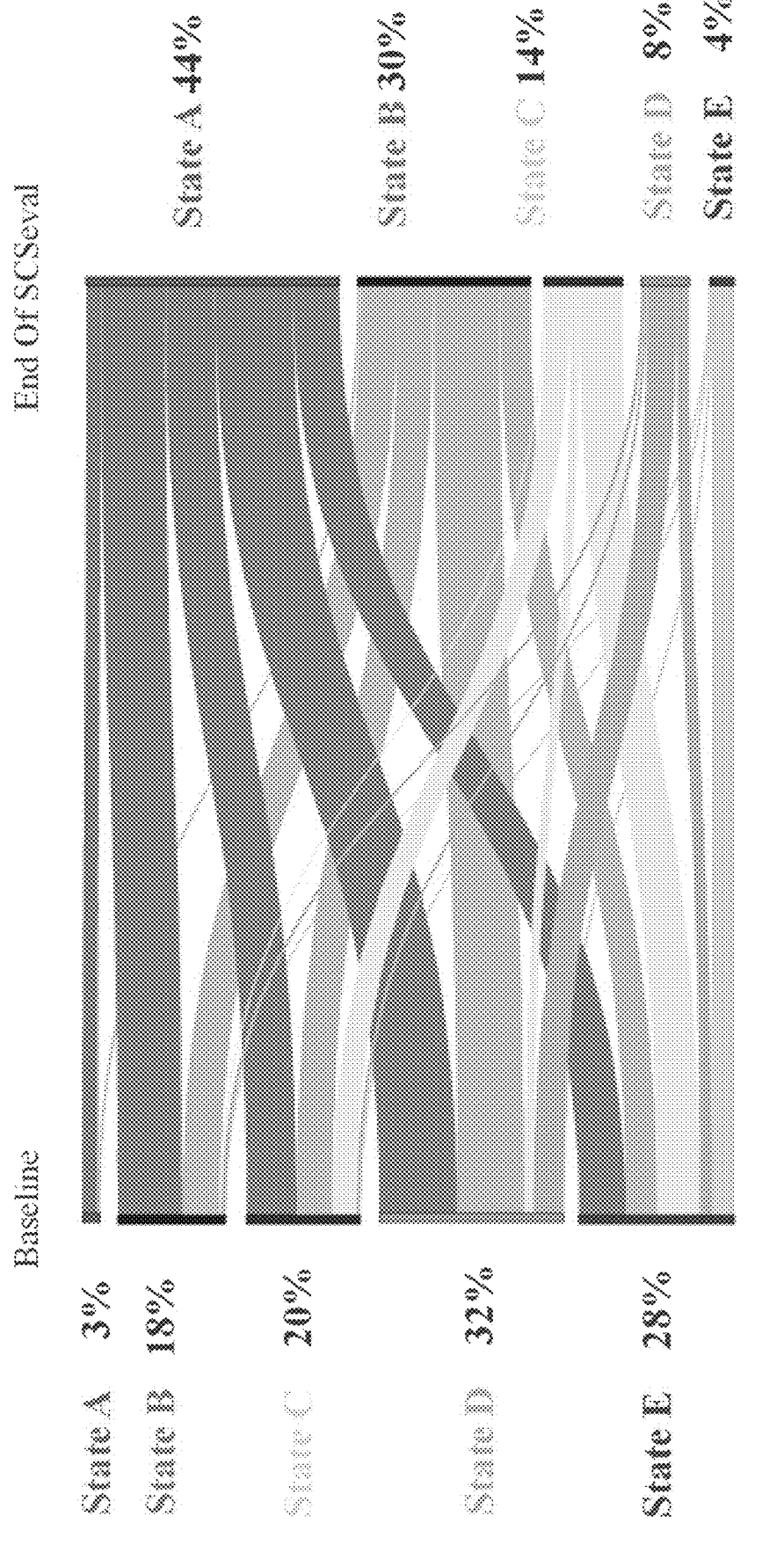
FIG. 6A illustrates an example visualization (population level) for representing population level metric data in accordance with aspects of the present disclosure.

FIG. 6A illustrates an example visualization 600 (population level) for representing population level metric data (e.g., trends in pain states) in accordance with aspects of the present disclosure. The visualization 600 may be implemented using any appropriate combination of colors, shading, graphics, notations, and the like.

The visualization 600 illustrates a transition of states over an observation period. In an example, the observation period may span from Baseline to End of SCSeval. In a non-limiting example, Baseline may correspond to 182 of the timeline 103 of FIG. 1C, and End of SCSeval may correspond to 185 of the timeline 103.

According to example aspects of the present disclosure, the visualization 600 illustrates the percentage of patients in each state (e.g., A through E) at Baseline, the percentage of patients in each state at End Of SCSeval, and the percentage of patients in each state at instances between Baseline and End of SCSeval. The visualization 600 may illustrate, for a population level, the state transitions between Baseline and End Of SCSeval. In some aspects, the system 100 may track, as illustrated in the examples included in visualization 600, which portions of a given percentage of patients in a given state (e.g., 32% patients in state D) transition to another state (e.g., state C) or remain in the same state.

Figure 6B:
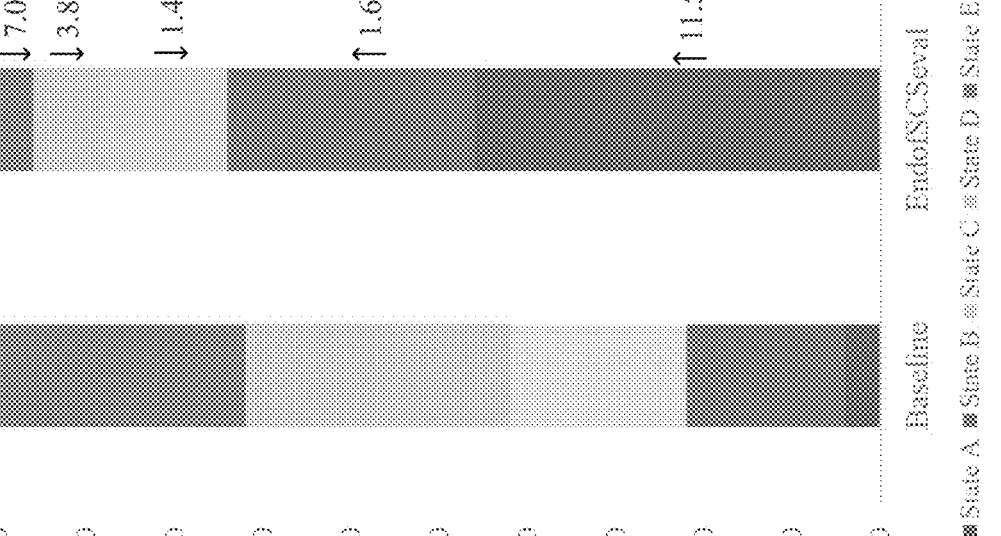
FIG. 6B illustrates an example visualization for representing change in state proportions over the observation period in accordance with aspects of the present disclosure.

FIG. 6B illustrates an example visualization 601 for representing change in state proportions over the observation period in accordance with aspects of the present disclosure. The visualization 601 may be implemented using any appropriate combination of colors, shading, graphics, notations, and the like.

According to example aspects of the present disclosure, the visualization 601 may illustrate the percentage of patients in each state (e.g., A through E) at Baseline, the percentage of patients in each state at End Of SCSeval, and includes an indication of respective increases or decreases in the percentages. For example, the visualization 601 includes an indication of a 11.5× increase in percentage of patients in state A and a 7.0× decrease in percentage of patients in state E.

Figure 7:
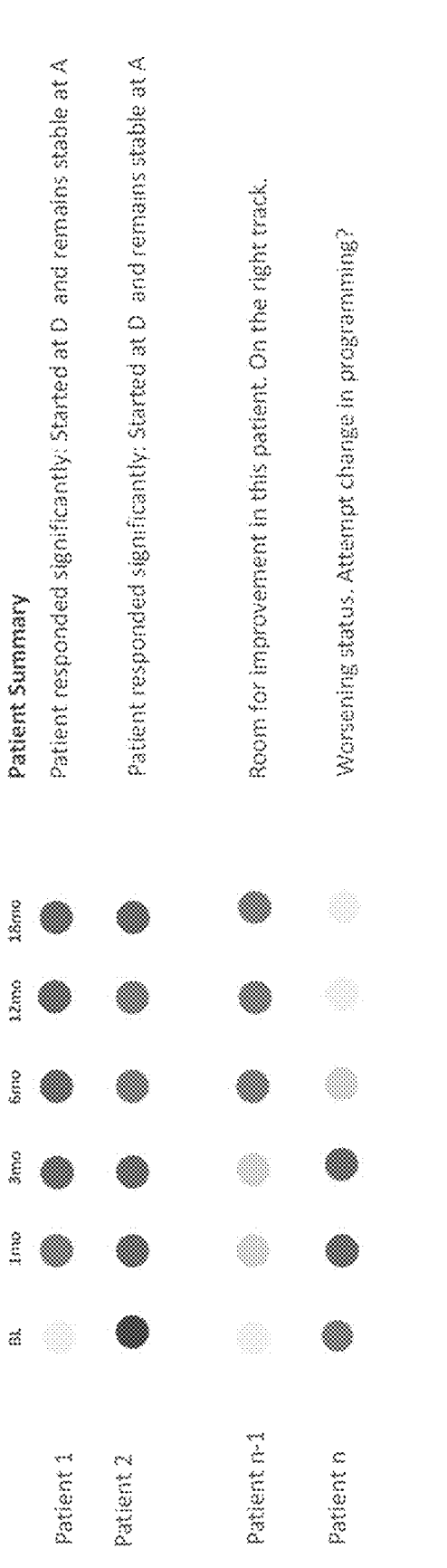
FIG. 7 illustrates an example of a visualization (patient level) for representing patient level metric data in accordance with aspects of the present disclosure.

FIG. 7 illustrates an example of a visualization 700 (patient level) for representing patient level metric data (e.g., trends in pain states) in accordance with aspects of the present disclosure. The visualization 700 may include a patient summary including trends in pain states (e.g., represented by colors and/or other appropriate indicators) and insightful recommendations. The visualization 700 may be implemented using any appropriate combination of colors, shading, graphics, notations, and the like. In some aspects, the visualization 700 may include different colors to represent respective states (e.g., A through E) described herein.

Tables 1 and 2 below illustrate example numerical values corresponding to pain states A through E in association with the seven domains (pain interference, ability to participate in social roles and activities, sleep disturbance, fatigue, depression, anxiety, and physical function) of the PROMIS-29 profile measure in accordance with aspects of the present disclosure.

TABLE 1

| | | | | | | |
|---|---|---|---|---|---|---|
| States characteristics | | | | | | |
| T-scores | | A | B | C | D | E |
| Anxiety | mean | 47.30 | 49.16 | 61.39 | 52.19 | 66.95 |
| | std | 7.01 | 7.11 | 4.07 | 7.20 | 5.53 |
| | median | 48.00 | 51.20 | 61.40 | 53.70 | 67.30 |
| | IQR | 13.40 | 15.50 | 3.90 | 9.70 | 7.80 |
| Depression | mean | 45.65 | 46.85 | 58.55 | 49.74 | 64.71 |
| | std | 6.15 | 6.30 | 4.36 | 6.29 | 5.57 |
| | median | 41.00 | 41.00 | 58.90 | 51.80 | 63.90 |
| | IQR | 8.00 | 10.80 | 6.50 | 12.90 | 7.20 |
| Fatigue | mean | 45.87 | 50.95 | 58.08 | 60.83 | 66.84 |
| | std | 6.47 | 5.84 | 5.44 | 6.42 | 6.02 |
| | median | 46.00 | 51.00 | 58.80 | 60.70 | 64.60 |
| | IQR | 5.50 | 6.50 | 7.60 | 7.60 | 8.90 |
| Pain Interference | mean | 53.31 | 62.53 | 64.54 | 69.99 | 72.33 |
| | std | 5.45 | 4.57 | 3.82 | 4.07 | 3.80 |
| | median | 55.60 | 61.20 | 65.20 | 69.70 | 75.60 |
| | IQR | 3.60 | 5.30 | 4.10 | 9.00 | 7.60 |
| Physical Function | mean | 44.62 | 37.40 | 36.04 | 32.30 | 31.46 |
| | std | 5.42 | 3.95 | 3.50 | 3.28 | 3.58 |
| | median | 43.50 | 36.70 | 35.60 | 31.90 | 31.90 |
| | IQR | 3.60 | 4.80 | 3.50 | 3.90 | 4.30 |
| Sleep Disturbance | mean | 44.49 | 51.25 | 55.29 | 59.31 | 64.42 |
| | std | 6.62 | 7.06 | 5.75 | 7.59 | 6.42 |
| | median | 46.20 | 52.40 | 54.30 | 59.80 | 63.80 |
| | IQR | 7.30 | 9.90 | 7.40 | 9.50 | 9.00 |

TABLE 1-continued

| States characteristics | | | | | | |
|---|---|---|---|---|---|---|
| T-scores | | A | B | C | D | E |
| Ability to | mean | 51.49 | 43.89 | 41.05 | 36.12 | 32.77 |
| Participate in | std | 6.02 | 4.65 | 3.94 | 4.70 | 4.61 |
| Social Roles | median | 51.90 | 44.20 | 42.30 | 37.30 | 34.00 |
| and Activities | IQR | 5.60 | 5.70 | 5.40 | 4.80 | 9.80 |

TABLE 2

| States characteristics | | | | | |
|---|---|---|---|---|---|
| Prop-r | A | B | C | D | E |
| mean | 0.48 | 0.27 | 0.17 | 0.11 | 0.03 |
| std | 0.13 | 0.06 | 0.05 | 0.06 | 0.04 |
| median | 0.45 | 0.27 | 0.16 | 0.12 | 0.02 |
| IQR | 0.14 | 0.08 | 0.06 | 0.09 | 0.06 |

FIGS. 8A through 8C are example diagrams illustrative of time agnostic K-means clustering used for model training in accordance with aspects of the present disclosure.

FIG. 8A includes an example plot 800 illustrative of clustering based on Baseline data and End Of Trial data to generate 5 states (e.g., least severity (A), most severity (E), where A>B>C>D>E) from 2898 data points. FIG. 8B includes an example plot 801 illustrative of individual PROMIS-29 question responses (in a 1-5 range of 1 to 5). FIG. 8C includes an example plot 802 illustrative of kernel clustering of pain states A through E with respect to the seven domains (pain interference, ability to participate in social roles and activities, sleep disturbance, fatigue, depression, anxiety, and physical function) of the PROMIS-29 profile measure.

FIGS. 9A and 9B illustrate example aspects of preliminary clinical decision interpretation for pain states in accordance with aspects of the present disclosure.

Referring to FIGS. 9A and 9B, the systems and techniques described herein support the conversion of mean T-scores into color coding to highlight the observations that can be derived based on state. The systems and techniques may support providing potential recommendations from the observations.

In some aspects, the systems and techniques may support using generative AI and/or rule based recommendations to provide the recommendations (e.g., based on determined state).

FIG. 10 illustrates an example of corroboration of state severity and pain intensity (PROPr) supported by aspects of the present disclosure.

Referring to FIG. 10, plot 1000 illustrates an example of pain intensity level distribution across states in accordance with aspects of the present disclosure. Plot 1001 illustrates an example of score (PROP-r score) distribution across states in accordance with aspects of the present disclosure.

FIGS. 11A and 11B illustrate example radar plots 1100 and 1101 supported by aspects of the present disclosure. The system 100 may provide graphical charts (e.g., radar plot 1100 and radar plot 1101) that may serve as visualizations to highlight which domains (also referred to herein as health domains) (e.g., fatigue, depression, anxiety, etc.) are most improved, and which domains have the most room for improvement. For example, referring to FIG. 11A, radar plot 1100 is illustrative of relative improvement in domains stratified (ranked) by states at the beginning of SCSeval. In another example, referring to FIG. 11B, radar plot 1101 is illustrative of relative improvement in domains stratified by states at the end of SCSeval.

Based on the information provided in radar plots 1100 and 1101 (and/or additional information derivable from the information in the radar plots 1100 and 1101), a clinician may identify and select actions (e.g., behavioral therapy, medication changes of SCS device programming, etc.) directed to improving one or more domains. For example, the clinician may select actions directed to improving the domains that have the most room for improvement.

FIG. 12 illustrates an example of a process flow 1200 in accordance with aspects of the present disclosure. In some examples, process flow 1200 may be implemented by aspects of a device (e.g., computing device 102, server 175, etc.) described herein.

In the following description of the process flow 1200, the operations may be performed in a different order than the order shown, or the operations may be performed in different orders or at different times. Certain operations may also be left out of the process flow 1200, or one or more operations may be repeated, or other operations may be added to the process flow 1200.

It is to be understood that any appropriate device (e.g., computing device 102, another computing device 102 in communication with the computing device 102, a server 175, etc.) may perform the operations shown.

The process flow 1200 may be implemented by a system including: a processor; and a memory storing instructions thereon that, when executed by the processor, cause the processor to perform aspects of the process flow 1200.

At 1205, the process flow 1200 may include processing one or more baseline patient-provided answers included in a baseline pain history survey associated with a patient.

At 1210, the process flow 1200 may include processing one or more patient-provided answers (e.g., patient reported outcomes, etc.) in association with at least one health domain, wherein the at least one health domain is associated with one or more chronic conditions (e.g., chronic pain, etc.).

At 1215, the process flow 1200 may include outputting a notification based on a trend associated with the one or more states (e.g., pain states, chronic pain states) with respect to a temporal period, the notification including a request for the patient to provide one or more additional patient-provided answers.

In an example, the one or more patient-provided answers and the one or more states are associated with first temporal information. In some aspects, at 1220, the process flow 1200 may include determining (e.g., calculating, evaluating, or confirming) a trend associated with the one or more states and one or more second states, wherein determining the trend includes: processing one or more additional patient-provided answers in association with the at least one health domain and second temporal information; and determining the one or more second states based on processing the one or more additional patient-provided answers.

Referring to the notification and trends described with respect to 1215 and 1220, the digital health platform techniques described herein enables surveys to be sent to a patient, and the data collected enables the state based clinical decision support as described herein. In some example aspects, in response to determining the worsening of temporal trends (e.g., a patient goes from State A to State C (or State D), the systems and techniques may support automatically sending requests to the patient to answer further questions that can enable the clinical decision support algorithms described herein to get to the bottom of the issue and provide a more targeted response.

At 1225, the process flow 1200 may include determining one or more states of a patient in association with the at least one health domain based on processing the one or more patient-provided answers. Information describing the state (s) determined for the patient may be stored in one or more electronic data records associated with the patient (e.g., as part of the patient's health history) in memory 106 and/or the database 130. Given the sensitivity associated with the patient's information (e.g., state information), the electronic data records may be secured and/or encrypted for data security purposes.

In some aspects, determining the one or more states is based on metric information respective to a plurality of health domains including the at least one health domain.

In some aspects, the one or more states include a characterization of at least one of: an amount of chronic pain of the patient; and a phenotype of the chronic pain. For example, each state comprises of multiple domains as defined by the derived phenotype.

In some aspects, determining the one or more states is based at least in part on processing the one or more inputs, which may include the baseline patient-provided answers and/or device utilization information.

In some aspects, each of the one or more states is determined in association with a plurality of health domains including the at least one health domain.

At 1230, the process flow 1200 may include determining a rating associated with the at least one health domain based on the one or more patient-provided answers, wherein determining the one or more states of a patient is based on the rating.

In some aspects, determining the rating associated with the at least one health domain is based on processing the one or more additional patient-provided answers.

Referring to the determining of the one or more states and determining the rating, aspects of the present disclosure support collapsing multiple domains into one state. Based on patient-provided answers provided in association with a standard metric (e.g., PROMIS-29) as described herein, the systems and techniques described herein support characterizing multiple factors that are relevant to the health of a patient. The systems and techniques described herein may collapse multiple domains (and data associated with the domains) into states that characterize an amount of chronic pain and phenotype of chronic pain. A present disclosure support providing the states for clinical management/decision support.

Aspects of the process flow 1200 may be implemented using machine learning techniques described herein.

For example, at 1235, the process flow 1200 may include providing the one or more patient-provided answers to one or more machine learning models. At 1240, the process flow 1200 may include receiving an output from the one or more machine learning models in response to the one or more machine learning models processing the one or more patient-provided answers, wherein the output includes the one or more states, the one or more recommendations, profile information associated with the patient, or a combination thereof.

At 1245, the process flow 1200 may include at least one of: generating patient level metric data associated with the one or more states and the at least one health domain with respect to the patient; and generating population level metric data associated with the one or more states and the at least one health domain with respect to a plurality of patients, the plurality of patients including at least the patient. The terms "metric data," "outcome metric," and "quantified chronic-pain metric" may be used interchangeably herein.

At 1250, the process flow 1200 may include providing one or more recommendations associated with the patient based on the one or more states.

In some aspects, providing the one or more recommendations (at 1250) is based on the patient level metric data, the population level metric data, or both.

In some aspects, determining the one or more states (at 1225), providing the one or more recommendations (at 1250), or both is based on processing the one or more second patient-provided answers.

In some aspects, the one or more recommendations are associated with delivering therapy to the patient, the therapy including neuromodulation therapy. In some aspects, the therapy includes spinal cord stimulation. In some aspects, the therapy includes peripheral nerve stimulation. In some embodiments, the one or more recommendations may include a recommendation to not deliver a therapy to the patient. In some embodiments, the one or more recommendations may include identifying one or more aspects of the patient to treat and other aspects of the patient to not treat.

In some aspects, the one or more recommendations are associated with at least one of: some or more behaviors of the patient; posture information associated with the patient; one or more medications associated with the patient; one or more device settings associated with delivering therapy to the patient; device utilization information; and imaging data including location data of one or more device components for delivering the therapy to the patient.

In some aspects, providing the one or more recommendations is based on determining the trend (of 1220).

At 1255, the process flow 1200 may include generating a graphical chart (e.g., a radar plot, etc.) including a visualization of a set of states in association with a set of health domains, wherein the set of health domains includes the at least one health domain and the set of states includes the one or more states.

The graphical chart (e.g., radar plot) serves as a visualization to highlight which domains are most improved, and which domains have the most room for improvement. Armed with the information provided in (and/or derivable from) the graphical chart, clinicians can choose actions (e.g., behavioral therapy, medication changes of SCS device programming) to improve the domains that have the most room for improvement.

In some aspects, the process flow 1200 may include training a plurality of machine learning models based on a training data set associated with a plurality of reference patients, wherein the training data set includes a reference set of patient-provided answers in association with the at least one health domain. The process flow 1200 may include defining threshold values corresponding to a set of candidate states based on the training, wherein the one or more states is determined from among the set of candidate states. In an example, determining the one or more states, providing the one or more recommendations, or both is based on one or more machine learning models included in the plurality of machine learning models correlating the one or more patient-provided answers to the one or more states based on the threshold values.

FIG. 13 illustrates a timeline 1300 including examples of device data with respect to a temporal axis (X-axis). Based on the device data, the systems and techniques may determine objective measures of chronic pain and provide om recommendations, in accordance with aspects of the present disclosure.

The device data may include raw data recorded and provided by any appropriate device (e.g., computing device 102, therapy device 162 (for example, a SCS device), wearable device 170, etc.) described herein. In some cases, the systems and techniques described herein may include accessing the device data via an open standard file and data format (e.g., JSON) supportive of data interchange. The systems and techniques may include accessing the device data at any appropriate temporal instance. Additionally, or alternatively, the device may upload the device data to a server or database, and the systems and techniques may include accessing the device data from the server or database. In the example of FIG. 13, the device data may include any appropriate quantity of data logs (e.g., X months of data logs, X days of data logs, X hours of data logs, and the like) supportive of the analysis techniques of the present disclosure.

In some example implementations, the systems and techniques may include accessing the device data at an in-clinic follow-up and/or remotely (e.g., a remote visit). In some cases, the systems and techniques may include autonomously (e.g., based on trigger criteria) and/or semi-autonomously accessing the device data. In some aspects, the systems and techniques may include analyzing data logs associated with a defined temporal period (e.g., 72 hours of data logs)

Events Plot 1305 includes events respective to one or more stimulation groups. In the example of FIG. 13, Events Plot 1305 includes events respective to stimulation groups A through C (Red=Group A, Orange=Group B, Yellow=Group C). In the example, events associated with modifying stimulation amplitude (Stimulation Amplitude Modified) are represented by light blue lines. Events associated with modifying a group (Group Modified) are represented by dark blue lines. Events associated with turning stimulation on or off (Stim On/Off) are represented by green and red lines, respectively.

ECAP Amplitude Histogram 1310 includes ECAP amplitude with respect to the temporal axis. For example, ECAP Amplitude Histogram 1310 includes ECAP amplitude histograms at each hour, split into bins of 2.3 uV (e.g., Dark blue ECAP 0-2.3 uV, Royal Blue ECAP 2.3-4.6 uV, etc.). In the example of FIG. 13, the ECAP Amplitude Histogram 1310 includes 72 hours of logs, but is not limited thereto.

Stimulation Amplitude Histogram 1315 includes stimulation amplitude with respect to the temporal axis. For example, Stim Amplitude Histogram 1315 includes stimulation amplitude at each hour within a temporal period (e.g., 72 hours of logs), split into bins depending on maximum stimulation amplitude. In the example of FIG. 13, bins are 0.64 mA in size.

Increase/Decrease/Hold (Algorithm State) Histogram 1320 includes states of a therapy algorithm (e.g., stimulation algorithm) with respect to the temporal axis. In the example of FIG. 13, royal blue=default, light blue=increase, red=decrease, yellow=hold. In the example of FIG. 13, the Increase/Decrease/Hold Histogram 1320 includes 720 hours of logs, but is not limited thereto.

CL Suspended Plot 1325 includes indications of whether a therapy algorithm (e.g., stimulation algorithm) is suspended, temporal information associated with the suspension of the therapy algorithm, and the reason for suspending the therapy algorithm (e.g., recharge, noise, cycling, etc.). In the example of FIG. 13, recharge is red, noise is blue, cycling is yellow. In the example case of FIG. 13, the therapy algorithm is suspended due to recharge at the temporal instances indicated in CL Suspended Plot 1325.

Statistics Plot 1330 includes statistical information with respect to the temporal axis. For example, Statistics Plot 1330 includes a plot of min/max stimulation amplitude (e.g., blue solid line) and min/max/median/mode ECAP amplitude (e.g., orange dotted line) at each hour within a temporal period (e.g., 720 hours of logs). In the example case of FIG. 13, as illustrated at Statistics Plot 1330, ECAP amplitude spikes when recharging (e.g., due to recharge noise) prior to recharge state being detected.

Posture Log 1335 includes histograms of posture by hour. Non-limiting examples of postures associated with the histograms include laying on back, laying on left side, laying on front, laying on right side, upright (e.g., standing or sitting), active, reclining, and unknown.

Recharge Log 1340 includes recharge events with respect to the temporal axis. In an example, Recharge Log 1340 includes shapes (e.g., box, rectangle, etc.) respectively representing characteristics of each recharge session. In the example of FIG. 13, the shape is a rectangle, and the width of each rectangle (e.g., along the Y-axis) represents the length of the corresponding recharge session. The bottom of the rectangle represents start percentage (e.g., percentage charged) at the start of the recharge session, and the top of the rectangle represents the end percentage of the recharge session.

Resting Trend Count 1345 is incremented every time the patient moves from one lying position to another lying position. The systems and techniques described herein support viewing the trend with respect to a target period (e.g., in the last 30 days) and specifying the time of interest (e.g., from 10 μm to 8 am).

Time Trend 1350 includes an indication of day and night periods. In an example, the systems described herein support converting a 24 hour time period into 8 hour or 12 hour periods as Day/Night, using different indicators (e.g., color) respectively corresponding to Day and Night.

According to example aspects of the present disclosure, using the device data and the example analyses (e.g., Events Plot 1305, ECAP Amplitude Histogram 1310, Stimulation Amplitude Histogram 1315, etc.) described with reference to FIG. 13, the systems and techniques described herein may support analysis of therapy programming, programming settings, programming effectiveness, and other factors associated with the programming.

In an example implementation, based on the device data and the example analyses, the systems and techniques may support identifying instances of manual switching between programming. For example, the systems and techniques may support identifying how many times the programming was changed per week. In another example, the systems and techniques may support identifying an initial few days with multiple changes, followed by an eventual settling on a therapy programming setting. In some aspects, the systems and techniques may associate multiple changes as being indicative of therapy ineffectiveness.

In some example implementations, the systems and techniques may support identifying additional conditions associated with programming changes. For example, the systems and techniques may include identifying and associating temporal information (e.g., Morning? Evening? Night?) and/or specific body positions with changes in therapy programming. In some other examples, the systems and techniques may include identifying and associating changes in amplitude (e.g., increases in stimulation amplitude) with changes in therapy programming. In some other cases, the systems and techniques may include associating therapy ineffectiveness with changes in therapy programming.

FIGS. 14A through 14C illustrate examples of clinical metrics derivable from device data described herein in accordance with aspects of the present disclosure. FIGS. 14A through 14C illustrate examples of population therapy trends over a temporal period of 6 months.

In some aspects, the systems and techniques may include acquiring the device data through data processing of open standard files (e.g., JSON files) from device uploads as described herein. The systems and techniques may support generating trends over a follow-up period and/or predicting trends based on the device data. In some example implementations, the systems and techniques may support determining potential implications of the observations.

Metrics 1405 includes lead location (% lead locations per thoracic level).

Metrics 1410 includes Programmed Location (% Programming Anode, Cathode).

Metrics 1415 includes ECAP Sensing Location (% Programming Anode, Cathode).

Metrics 1420 includes % Time spent in Stimulation. In an example, a case of majority time spent in stimulation may be an indicator of patient satisfaction and usage of SCS therapy.

Metrics 1425 includes % Time spent Recharging. In an example, a case of less time spent in recharge (e.g., 20 minutes/day) may be an indicator of increased optimization of therapy, lower battery usage, and reduced inconvenience related to recharging.

Metrics 1430 includes % Time in which a programming algorithm (also referred to herein as a therapy algorithm) is in decrease mode or hold Mode. Metrics 1430 indicates a % of time the algorithm is making changes (e.g., decrease or hold status). The changes (e.g., decrease, hold) may enable consistent dosing.

Metrics 1435 includes % Patients according to Stimulation Amplitude (e.g., expressed in mA) and/or stimulation amplitude range. In some aspects, lower stimulation amplitude may be an indicator of optimized therapy delivery.

Metrics 1440 includes % Patients according to ECAP amplitude (e.g., expressed in u V) and/or ECAP sensed range. In some aspects, ECAP amplitude may be an indicator for confirming whether a "Signal is viable to engage close-loop algorithm." In some aspects, ECAP amplitude may be indicative of overstimulation and/or the degree of overstimulation. Alternatively, the ECAP amplitude may be indicated of understimulation and/or the degree of understimulation.

In some aspects, the systems and techniques may include determining the stimulation amplitude and ECAP amplitude based on 72 hour summaries. In some other aspects, the systems and techniques may include determining the stimulation amplitude and ECAP amplitude based on other temporal periods (e.g., 720 hour (3 month) summaries).

Metrics 1445 includes % Time a patient is in a given Body Position (e.g., upright) or state (e.g., active, at rest, etc.). In some aspects, a case in which the amount of time a patient has spent upright and active over time is greater than the amount of time the patient has spent at rest may indicate improvement in the patient's functional status. In some aspects, the duration and time (e.g., in the evening) of less activity may be indicative that the patient may be having better rest and higher sleep quality, and may indicate an improvement in the patient's functional status.

Aspects of the present disclosure support representing any of the clinical metrics as a summary with respect to a temporal period (e.g., 3 month summary, 6 month summary, etc.). In some other aspects, aspects of the present disclosure support providing trend information (e.g., monthly trend, etc.) of any of the clinical metrics. In a non-limiting example, the time spent in stimulation and % time spent in recharging can be represented as a 6 month summary or as a monthly trend.

It should be clarified that some or all data (e.g., survey data, patient reported outcomes, application data, and/or digital health data) can be timestamped and synchronized with timestamped device data. If/when a patient changes device settings, the digital health platform may be prompted to gather pain information, patient surveys, or other forms of patient reported outcomes to coincide in time with the change in device settings. Understanding transition points can often be helpful in clustering/model training.

In addition to pre-determined time intervals and surveys, responses to the surveys and/or patient reported outcomes can dynamically influence the next survey interval and what surveys are selected. This could help us focus in on patient outcomes when the patient experiences a pain "flare" to see if the pain flare correlates with changes in ECAP response or activity (device data in general), for instance. Further still, recent device stimulation changes could be tagged for digital health data (e.g., surveys and/or patient reported outcomes) as this could help identify "wash in" and "wash out" periods that may have residual impacts on the survey data.

FIGS. 15A through 15C illustrate example associations between device based metrics and standard survey domains, supportive of determining objective measures of chronic pain from an implantable medical device and/or a wearable device in accordance with aspects of the present disclosure.

According to example aspects of the present disclosure, each PROMIS-29 domain and specific question as posed during a survey may be related to a specific device based metric. The systems and techniques described herein may support determining a device based metric based on a given question (e.g., "Are you able to do chores such as vacuuming or yard work?"), the corresponding PROMIS-29 domain+ "Physical Function"), and a patient-provided answer (e.g., any of 1 through 5) to the given question. The device based metric provides a quantifiable measure of the chronic pain status of the patient.

Example implementations supportive of determining states (e.g., mental states, physical states, etc.) and providing recommendations based on the states are described herein.

Example #1—Patient reports high pain score, and the device data indicates that the algorithm is decreasing below the target value for an unacceptable time and/or stimulation amount. In some aspects, cither report the device data and/or the analysis of the device data back to the clinical representative/physician and/or prompt user to make a change.

Example #2—Patient experiences satisfactory relief during the day, but worse pain at night. The systems and techniques may include determining the patient experiences based on one or more of patient reported outcomes, device data (e.g., accelerometer data), resting trend information, ECAP algorithm information, and the like described herein.

In an example implementation, the determined patient experiences may serve as a trigger for the digital health platform application to prompt the patient to answer one or more additional survey questions (e.g., ask about heavy legs, etc.) that may be indicative of high frequency (HF) overstimulation.

In some aspects, the digital health platform application may output a notification prompting the user to perform one or more actions/alter patient behavior. For example, the digital health platform application may prompt the user to decrease therapy/change to a night group/set up a night group for the patient through a step-by-step process. The digital health platform application may provide a prompt asking whether the patient wants therapy to be adjusted and, in the affirmative, a manner in which the therapy is to be adjusted and/or a criteria based on which the therapy is to be adjusted. For example, the prompt may include an inquiry asking whether the patient wants the therapy to be automatically adjusted between certain hours and/or conditionally adjusted in response to an accelerometer input (e.g., compared to a threshold accelerometer value).

In some additional and/or alternative aspects, the digital health platform may generate and transmit a message to the clinical representative/physician, and the message may include an indication that the patient may benefit from different programming at night.

Example #3—Patient reports a new high pain score, algorithm performance changes (e.g., much more active, increases in stimulation activity, etc.), the maximum recorded ECAP changes, and/or the ECAP shape or metrics (e.g., principal component analysis (PCA) values) changes.

In an example, the techniques described herein may determine, based on an analysis of the accelerometer data and the stimulation programming, whether lead migration has potentially occurred or whether to recommend reprogramming.

For example, based on accelerometer data indicating that the patient is more active compared to a previous period, and device data indicating that the stimulation programming is unchanged, the techniques described herein may include generating an alert indicating that lead migration has occurred and/or recommend reprogramming.

Example #4—The systems and techniques may support acquiring a holistic measure (e.g., based on any appropriate combination of data described herein) of the patient state and tracking changes of the holistic measure over time. For example, the systems and techniques described herein may include acquiring and tracking the holistic measure over time after a permanent SCS implant operation (e.g., after therapy healing/wound check).

In some aspects, the systems and techniques may include comparing the holistic measure to wearable device data and trial device data, for example, to show improvements. In some cases, the systems and techniques may utilize the holistic measure to demonstrate the benefits or value of a proposed recommendation (e.g., therapy reprogramming, therapy recommendations, etc.).

In some aspects, the digital health platform application may output a notification prompting medical personnel to implement device reprogramming for cases in which the holistic measure deviates from a target value for an extended period of time (e.g., longer than a threshold duration). That is, for example, large deviations for an unacceptable time may trigger rep/physician alert for reprogramming.

In some aspects, the digital health platform application may suggest changes to therapy settings based on the holistic measure, the wearable device data, and/or the trial device data. Non-limiting examples of therapy settings include cycling or endurance settings (e.g., for battery longevity).

Example #5—The systems and techniques may support recent time trends of group usage.

Example #6—The systems and techniques may support monitoring activity patterns based on wearable device data. For example, based on accelerometer data, the systems and techniques may support identifying changes in activity level (e.g., increased physical activity, decreased physical activity, etc.) of a patient. In an example, a patient may be highly active after recovering from a physical condition (e.g., chronic pain) and/or mental condition (e.g., depression) preventing the patient from engaging in activities. In response to detecting the change in activity level of the patient, the digital health platform application may generate a prompt including follow up questions (e.g., "Is in the increase in activity due to X?") for the patient.

FIG. 16 illustrates an example of a process flow 1600 in accordance with aspects of the present disclosure. In some examples, process flow 1600 may be implemented by aspects of a device (e.g., computing device 102, server 175, etc.) described herein.

In the following description of the process flow 1600, the operations may be performed in a different order than the order shown, or the operations may be performed in different orders or at different times. Certain operations may also be left out of the process flow 1600, or one or more operations may be repeated, or other operations may be added to the process flow 1600.

It is to be understood that any appropriate device (e.g., computing device 102, another computing device 102 in communication with the computing device 102, a server 175, etc.) may perform the operations shown.

The process flow 1600 may be implemented by a system including: a processor; and a memory storing instructions thereon that, when executed by the processor, cause the processor to perform aspects of the process flow 1600.

At 1605, the process flow 1600 may include determining one or more states of a patient based on processing: one or more patient-provided answers associated with at least one health domain; and data from one or more devices associated with providing treatment to the patient or monitoring the patient.

In some aspects, the one or more states include a mental state, a physical state, or both.

In some aspects, the one or more states are determined in association with: the at least one health domain; at least one second health domain different from the at least one health domain; or a combination thereof.

In some aspects, the one or more states are determined based on an association between the one or more patient-provided answers, the data from the one or more devices, and the one or more states.

In some aspects, the one or more devices include a therapy device providing therapy to the patient, and the data includes one or more stimulation parameters (e.g., amplitude, frequency, contacts, pulse width, method to of achieving charge balance, etc.) associated with providing the therapy to the patient.

In some aspects, the one or more devices include a therapy device providing therapy to the patient, and the data includes at least one of: battery charging activity associated with the therapy device; programming activity associated with the therapy device; and reprogramming activity associated with the therapy device.

In some aspects, the one or more devices include a therapy device providing stimulation to the patient; and the data includes an amplitude, a variation in the amplitude, or both of a data signal received by the therapy device, wherein the data signal includes an evoked compound action potential (ECAP) signal, an evoked compound muscle action potential (ECMAP) signal, or both. In some aspects, the one or more devices may record one or more other suitable physiological signals such as, for example, far-field cardiac activity, muscle activity, and baseline local neural activity.

In some aspects, the one or more devices include a wearable device, and the data includes at least one of: physiological data of the patient; motion data associated with the patient; and posture data associated with the patient.

In some aspects, the one or more devices include an implanted stimulation device.

In some aspects, the one or more patient-provided answers include one or more patient reported outcomes associated with a predefined survey.

In some aspects, determining the one or more states is based on determining one or more trends associated with the data with respect to a temporal period.

At 1610, the process flow 1600 may include outputting a notification based at least in part the one or more patient-provided answers, the notification including a request for the patient to provide one or more second patient-provided answers associated with the at least one health domain, at least one second health domain, or both.

At 1615, the process flow 1600 may include confirming the one or more states based on processing the one or more second patient-provided answers.

At 1620, the process flow 1600 may include providing one or more recommendations associated with the patient based on the one or more states.

In some aspects, the one or more recommendations include one or more recommended patient behaviors.

In some aspects, the one or more recommendations include one or more recommended operational parameters associated with the one or more devices.

In some aspects, the one or more recommendations include one or more recommended device parameters associated with delivering therapy to the patient.

In some aspects, the one or more recommendations are provided in association with: the at least one health domain; at least one second health domain different from the at least one health domain; or a combination thereof.

The process flows described herein (and/or one or more operations thereof) may be carried out or otherwise performed, for example, by at least one processor. The at least one processor may be the same as or similar to the processor(s) 104 of the computing device 102 described above. A processor other than any processor described herein may also be used to execute the process flows. The at least one processor may perform operations of the process flows by executing elements stored in a memory (e.g., memory 106, memory 165, etc.). The elements stored in memory and executed by the processor may cause the processor to execute one or more operations of a function as shown in the process flows. One or more portions of the process flows may be performed by the processor executing any of the contents of memory.

As noted above, the present disclosure encompasses methods with fewer than all of the steps identified in the process flows described herein, as well as methods that include additional steps beyond those identified in the process flows. The present disclosure also encompasses methods that include one or more steps from one method described herein, and one or more steps from another method described herein. Any correlation described herein may be or include a registration or any other correlation.

The foregoing is not intended to limit the disclosure to the form or forms disclosed herein. In the foregoing Detailed Description, for example, various features of the disclosure are grouped together in one or more aspects, implementations, and/or configurations for the purpose of streamlining the disclosure. The features of the aspects, implementations, and/or configurations of the disclosure may be combined in alternate aspects, implementations, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, implementation, and/or configuration. Thus, the following claims are hereby incorporated into this Detailed Description, with each claim standing on its own as a separate preferred implementation of the disclosure.

Moreover, though the foregoing has included description of one or more aspects, implementations, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, implementations, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

Example Aspects of the Present Disclosure Include:

A system including: a processor; and a memory storing instructions thereon that, when executed by the processor, cause the processor to: process one or more patient-provided answers in association with at least one health domain, wherein the at least one health domain is associated with one or more chronic conditions; determine one or more states of a patient in association with the at least one health domain based at least in part on processing the one or more patient-provided answers; and provide one or more recommendations associated with the patient based at least in part on the one or more states.

Any of the aspects herein, wherein determining the one or more states is based on metric information respective to a plurality of health domains including the at least one health domain.

Any of the aspects herein, wherein the one or more states include a characterization of at least one of: an amount of chronic pain of the patient; and a phenotype of the chronic pain.

Any of the aspects herein, wherein the instructions are further executable by the processor to: determine a rating associated with the at least one health domain based at least in part on the one or more patient-provided answers, wherein determining the one or more states of a patient is based at least in part on the rating.

Any of the aspects herein, wherein the instructions are further executable by the processor to: output a notification based at least in part on a trend associated with the one or more states with respect to a temporal period, the notification including at least one of: a request for the patient to provide one or more additional patient-provided answers; and a request for medical personnel to provide input; and determine a rating associated with the at least one health domain based on processing the one or more additional patient-provided answers, the input, or both.

Any of the aspects herein, wherein the instructions are further executable by the processor to: provide the one or more patient-provided answers to one or more machine learning models; and receive an output from the one or more machine learning models in response to the one or more machine learning models processing the one or more patient-provided answers, wherein the output includes the one or more states, the one or more recommendations, profile information associated with the patient, or a combination thereof.

Any of the aspects herein, wherein the instructions are further executable by the processor to: train a plurality of machine learning models based at least in part on a training data set associated with a plurality of reference patients, wherein the training data set includes a reference set of patient-provided answers in association with the at least one health domain; and define threshold values corresponding to a set of candidate states based at least in part on the training, wherein the one or more states are determined from among the set of candidate states, wherein determining the one or more states, providing the one or more recommendations, or both is based at least in part on one or more machine learning models included in the plurality of machine learning models correlating the one or more patient-provided answers to the one or more states based at least in part on the threshold values.

Any of the aspects herein, wherein: the one or more patient-provided answers and the one or more states are associated with first temporal information; and the instructions are further executable by the processor to: determine a trend associated with the one or more states and the one or more additional states, wherein determining the trend includes: processing one or more second patient-provided answers in association with the at least one health domain and second temporal information; and determining the one or more second states based at least in part on processing the one or more second patient-provided answers, wherein providing the one or more recommendations is based at least in part on determining the trend.

Any of the aspects herein, wherein the instructions are further executable by the processor to: generate a graphical chart including a visualization of a set of states in association with a set of health domains, wherein the set of health domains includes the at least one health domain and the set of states includes the one or more states.

Any of the aspects herein, wherein: each of the one or more states is determined in association with a plurality of health domains including the at least one health domain.

Any of the aspects herein, wherein the one or more recommendations are associated with at least one of: one or more behaviors of the patient; posture information associated with the patient; one or more medications associated with the patient; one or more device settings associated with delivering therapy to the patient; and imaging data including location data of one or more device components for delivering the therapy to the patient.

Any of the aspects herein, wherein the instructions are further executable by the processor to: process one or more baseline patient-provided answers included in a baseline pain history survey associated with the patient, wherein determining the one or more states, providing the one or more recommendations, or both is based at least in part on processing the one or more baseline patient-provided answers.

Any of the aspects herein, wherein the instructions are further executable by the processor to at least one of: generate patient level metric data associated with the one or more states and the at least one health domain with respect to the patient; and generate population level metric data associated with the one or more states and the at least one health domain with respect to a plurality of patients, the plurality of patients including at least the patient, wherein providing the one or more recommendations is based at least in part on the patient level metric data, the population level metric data, or both.

Any of the aspects herein, wherein the one or more recommendations are associated with delivering therapy to the patient, the therapy including neuromodulation therapy.

Any of the aspects herein, wherein the therapy includes spinal cord stimulation.

Any of the aspects herein, wherein the therapy includes peripheral nerve stimulation.

A method including: processing one or more patient-provided answers in association with at least one health domain, wherein the at least one health domain is associated with one or more chronic conditions; determining one or more states of a patient in association with the at least one health domain based at least in part on processing the one or more patient-provided answers; and providing one or more recommendations associated with the patient based at least in part on the one or more states.

Any of the aspects herein, wherein the one or more states indicate an amount of chronic pain of the patient in association with the at least one health domain.

Any of the aspects herein, further including: generating profile information associated with the patient, the profile information including an indication of the one or more states, wherein providing the one or more recommendations is based at least in part on the profile information.

A non-transitory computer readable medium including instructions, which when executed by a processor: process one or more patient-provided answers in association with at least one health domain, wherein the at least one health domain is associated with one or more chronic conditions; determine one or more states of a patient in association with the at least one health domain based at least in part on processing the one or more patient-provided answers; and provide one or more recommendations associated with the patient based at least in part on the one or more states.

A system including: a processor; and a memory storing instructions thereon that, when executed by the processor, cause the processor to: determine one or more states of a patient based at least in part on processing: one or more patient-provided answers associated with at least one health domain; and data from one or more devices associated with providing treatment to the patient or monitoring the patient; and provide one or more recommendations associated with the patient based at least in part on the one or more states.

Any of the aspects herein, wherein the one or more recommendations include one or more recommended patient behaviors.

Any of the aspects herein, wherein the one or more recommendations include one or more recommended operational parameters associated with the one or more devices.

Any of the aspects herein, wherein the one or more recommendations include one or more recommended device parameters associated with delivering therapy to the patient.

Any of the aspects herein, wherein the one or more states include a mental state, a physical state, or both.

Any of the aspects herein, wherein the one or more devices include a therapy device providing therapy to the patient, and the data includes one or more stimulation parameters associated with providing the therapy to the patient.

Any of the aspects herein, wherein the one or more devices include a therapy device providing therapy to the patient, and the data includes at least one of: battery charging activity associated with the therapy device; programming activity associated with the therapy device; and reprogramming activity associated with the therapy device.

Any of the aspects herein, wherein: the one or more devices include a therapy device providing stimulation to the patient; and the data includes an amplitude, a variation in the amplitude, or both of a data signal received by the therapy device, wherein the data signal includes an evoked compound action potential (ECAP) signal, an evoked compound muscle action potential (ECMAP) signal, or both.

Any of the aspects herein, wherein the one or more devices include a wearable device, and the data includes at least one of: physiological data of the patient; motion data associated with the patient; and posture data associated with the patient.

Any of the aspects herein, wherein the one or more devices include an implanted stimulation device.

Any of the aspects herein, wherein the one or more states are determined in association with: the at least one health domain; at least one second health domain different from the at least one health domain; or a combination thereof.

Any of the aspects herein, wherein the one or more recommendations are provided in association with: the at least one health domain; at least one second health domain different from the at least one health domain; or a combination thereof.

Any of the aspects herein, wherein the one or more states are determined based at least in part on an association between the one or more patient-provided answers, the data from the one or more devices, and the one or more states.

Any of the aspects herein, wherein the instructions are further executable by the processor to: output a notification based at least in part processing the one or more patient-provided answers, the notification including a request for the patient to provide one or more second patient-provided answers associated with the at least one health domain, at least one second health domain, or both; and confirming the one or more states based at least in part on processing the one or more second patient-provided answers.

Any of the aspects herein, wherein the one or more patient-provided answers include one or more patient reported outcomes associated with a predefined survey.

Any of the aspects herein, wherein determining the one or more states is based at least in part on determining one or more trends associated with the data with respect to a temporal period.

A method including: determining one or more states of a patient based at least in part on processing: one or more patient-provided answers associated with at least one health domain; and data from one or more devices associated with providing treatment to the patient or monitoring the patient; and providing one or more recommendations associated with the patient based at least in part on the one or more states.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/implementations in combination with any one or more other aspects/features/implementations.

Use of any one or more of the aspects or features as disclosed herein.

It is to be appreciated that any feature described herein can be claimed in combination with any other feature(s) as described herein, regardless of whether the features come from the same described implementation.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an implementation that is entirely hardware, an implementation that is entirely software (including firmware, resident software, micro-code, etc.) or an implementation combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

What is claimed is:

1. A system, comprising:
a medical device implanted into a patient;
a processor; and
a memory storing instructions thereon that, when executed by the processor, cause the processor to:
   prompt the patient, at a plurality of predetermined time intervals, to respond to a set of survey questions to yield patient-provided answers;
   process, using one or more machine learning models, one or more inputs including the patient-provided answers and device utilization information of a wearable device and the medical device in association with at least one health domain, wherein the at least one health domain is associated with one or more chronic conditions;
   determine, based on an output from the one or more machine learning models, one or more states of the patient comprising a phenotype of an amount of chronic pain experienced by the patient;
   adjust, based on the one or more states, one or more operating parameters of the medical device; and
   store information describing the one or more states in an electronic data record.

2. The system of claim 1, wherein determining the one or more states is based on metric information respective to a plurality of health domains comprising the at least one health domain, the instructions further enabling the processor, when executed, to:
   provide one or more recommendations associated with the patient based at least in part on the one or more states.

3. The system of claim 2, wherein the one or more states further comprise a characterization of:
an amount of chronic pain of the patient.

4. The system of claim 2, wherein the instructions are further executable by the processor to:
   determine a rating associated with the at least one health domain based at least in part on the patient-provided answers,
   wherein determining the one or more states of the patient is based at least in part on the rating.

5. The system of claim 2, wherein the instructions are further executable by the processor to:
   output a notification based at least in part on a trend associated with the one or more states with respect to a temporal period, the notification comprising at least one of:
      a request for the patient to provide one or more additional patient-provided answers; and
      a request for medical personnel to provide input; and
   determine a rating associated with the at least one health domain based on processing the one or more additional patient-provided answers, the input, or both.

6. The system of claim 2, wherein
the output from the one or more machine learning models in response to the one or more machine learning models processing the patient-provided answers further comprises the one or more recommendations, profile information associated with the patient, or a combination thereof.

7. The system of claim 2, wherein the instructions are further executable by the processor to:
   train a plurality of machine learning models based at least in part on a training data set associated with a plurality of reference patients, wherein the training data set comprises a reference set of patient-provided answers in association with the at least one health domain; and
   define threshold values corresponding to a set of candidate states based at least in part on the training, wherein the one or more states are determined from among the set of candidate states,
   wherein determining the one or more states, providing the one or more recommendations, or both is based at least in part on the one or more machine learning models included in the plurality of machine learning models correlating the patient-provided answers to the one or more states based at least in part on the threshold values.

8. The system of claim 2, wherein:
the one or more states are associated with first temporal information; and
the instructions are further executable by the processor to:
   determine a trend associated with the one or more states and one or more additional states, wherein determining the trend comprises:
      processing one or more second inputs including at least one of second patient-provided answers and second device utilization information in association with the at least one health domain and second temporal information; and
      determining one or more second states based at least in part on processing the one or more second inputs,
   wherein providing the one or more recommendations is based at least in part on determining the trend.

9. The system of claim 2, wherein the instructions are further executable by the processor to:
   generate a graphical chart comprising a visualization of a set of states in association with a set of health domains, wherein the set of health domains comprises the at least one health domain and the set of states comprises the one or more states.

10. The system of claim 2, wherein:
each of the one or more states is determined in association with a plurality of health domains comprising the at least one health domain.

11. The system of claim 2, wherein the one or more recommendations are associated with at least one of:
   one or more behaviors of the patient;
   posture information associated with the patient;
   one or more medications associated with the patient;
   one or more device settings associated with delivering therapy to the patient;
   the device utilization information; and
   imaging data comprising location data of one or more device components for delivering the therapy to the patient.

12. The system of claim 2, wherein the instructions are further executable by the processor to:
   process one or more baseline patient-provided answers comprised in a baseline pain history survey associated with the patient, wherein determining the one or more states, providing the one or more recommendations, or both is based at least in part on processing the one or more baseline patient-provided answers.

13. The system of claim 2, wherein the instructions are further executable by the processor to at least one of:

generate patient level metric data associated with the one or more states and the at least one health domain with respect to the patient; and generate population level metric data associated with the one or more states and the at least one health domain with respect to a plurality of patients, the plurality of patients comprising at least the patient, wherein providing the one or more recommendations is based at least in part on the patient level metric data, the population level metric data, or both.

14. The system of claim 2, wherein the one or more recommendations are associated with delivering therapy to the patient, the therapy comprising a neuromodulation therapy.

15. The system of claim 14, wherein the therapy comprises spinal cord stimulation.

16. The system of claim 14, wherein the therapy comprises peripheral nerve stimulation.

17. A method, comprising:

prompting a patient, at a plurality of predetermined time intervals, to respond to a set of survey questions to yield patient-provided answers;

processing, using one or more machine learning models, one or more inputs including the patient-provided answers and device utilization information of a wearable device and a medical device implanted in the patient in association with at least one health domain, wherein the at least one health domain is associated with one or more chronic conditions;

determining, based on an output from the one or more machine learning models, one or more states of the patient comprising a phenotype of an amount of chronic pain experienced by the patient;

adjusting, based on the one or more states, one or more operating parameters of the medical device; and storing information describing the one or more states in an electronic data record.

18. The method of claim 17, wherein the one or more states further indicate an amount of chronic pain of the patient in association with the at least one health domain, the method further comprising:

providing one or more recommendations associated with the patient based at least in part on the one or more states.

19. The method of claim 18, further comprising:

generating profile information associated with the patient, the profile information comprising an indication of the one or more states, wherein providing the one or more recommendations is based at least in part on the profile information.

20. A non-transitory computer readable medium comprising instructions, which when executed by a processor:

prompt a patient, at a plurality of predetermined time intervals, to respond to a set of survey questions to yield patient-provided answers;

process, using one or more machine learning models, one or more inputs including the patient-provided answers and device utilization information of a wearable device and a medical device implanted in the patient in association with at least one health domain, wherein the at least one health domain is associated with one or more chronic conditions;

determine, based on an output from the one or more machine learning models, one or more states of the patient comprising a phenotype of an amount of chronic pain experienced by the patient;

adjust, based on the one or more states, one or more operating parameters of the medical device; and store information describing the one or more states in an electronic data record.

* * * * *